US008020343B2

(12) United States Patent
Pearce et al.

(10) Patent No.: US 8,020,343 B2
(45) Date of Patent: *Sep. 20, 2011

(54) ENHANCED SHELF LIFE AND ON SEED STABILIZATION OF LIQUID BACTERIUM INOCULANTS

(75) Inventors: Jeremy David Pearce, Bosham (GB); Mary Ann Carpenter, Littlehampton (GB); R. D. Piran Cargeeg, Saskatoon (CA); Guoping Yang, Saskatoon (CA)

(73) Assignee: Becker Underwood Inc., Ames, IA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/473,604

(22) Filed: Jun. 23, 2006

(65) Prior Publication Data
US 2007/0074451 A1   Apr. 5, 2007

Related U.S. Application Data

(63) Continuation-in-part of application No. 11/020,714, filed on Dec. 23, 2004.

(51) Int. Cl.
*A01C 1/06* (2006.01)
*A01C 21/00* (2006.01)

(52) U.S. Cl. ........................................................ 47/57.6
(58) Field of Classification Search .................. 47/57.6
See application file for complete search history.

(56) References Cited

U.S. PATENT DOCUMENTS

| 4,337,077 | A | | 6/1982 | Rutherford | 71/9 |
| 4,367,609 | A | * | 1/1983 | Lloyd | 47/57.6 |
| 4,849,005 | A | | 7/1989 | Williams et al. | 71/7 |
| 4,875,921 | A | | 10/1989 | Paau | 71/7 |
| 4,886,664 | A | * | 12/1989 | Jung et al. | 424/93.4 |
| 5,137,747 | A | * | 8/1992 | Malandain et al. | 427/4 |
| 5,292,507 | A | | 3/1994 | Charley | 424/93 K |
| 5,695,541 | A | * | 12/1997 | Kosanke et al. | 71/7 |
| 5,697,186 | A | | 12/1997 | Neyra et al. | 47/57.6 |
| 5,916,029 | A | * | 6/1999 | Smith et al. | 47/57.6 |
| 6,606,822 | B2 | * | 8/2003 | Bonfiglio | 47/57.6 |
| 6,610,531 | B1 | | 8/2003 | Mateczun et al. | 435/260 |
| 6,698,137 | B2 | | 3/2004 | Muhr | 47/57.6 |
| 7,022,649 | B2 | | 4/2006 | Magri | 504/117 |
| 2002/0050096 | A1 | | 5/2002 | Bonfiglio | 47/57.6 |
| 2002/0058327 | A1 | | 5/2002 | Loh et al. | 435/252.2 |
| 2002/0104262 | A1 | | 8/2002 | Muhr | 47/57.6 |
| 2003/0060496 | A1 | | 3/2003 | Merritt et al. | 514/383 |
| 2003/0228679 | A1 | | 12/2003 | Smith et al. | 435/235.1 |
| 2004/0081714 | A1 | | 4/2004 | Pauly et al. | 424/774 |
| 2004/0092400 | A1 | | 5/2004 | Lucio Magri | 504/117 |
| 2004/0102328 | A1 | | 5/2004 | Johnson et al. | 504/350 |

FOREIGN PATENT DOCUMENTS

| EP | 0 203 708 | | 6/1991 |
| EP | 0 410 862 | B1 | 7/1995 |
| RU | 2052507 | C1 | 1/1996 |
| SU | 1673973 | A1 | 8/1991 |

OTHER PUBLICATIONS

"SeedQuest News" (news release Mar. 22, 2001)(2 pages total).*
Streeter,J "Effect of trehalose on survival of *Bradyrhizobium japonicum* during desiccation," Journal of Applied Microbiology, 2003, 95, pp. 484-491.*
Singleton et al.; "Development and Evaluation of Liquid Inoculants," ACIAR Proceedings 109e, 2002, pp. 52-66.*
Dandekar et al. "*Agrobacterium*-mediated transformation of somatic embryos as a method for the production of transgenic plants," Journal of Tissue Culture Methods, vol. 12, No. 4, pp. 145-150, 1989.*
Large Soviet Encyclopedia, 1972, vol. 8, p. 133.
Juan Carlos Argüelles, "Physiological Roles of Trehalose in Bacteria and Yeast: a Comparative Analysis," Arch Microbiol (2000) 174:217-224.
Crowe, et al., "Preservation of Membranes in Anhydrobiotic Organisms: The Role of Trehalose," Science, New Series, vol. 223. No. 4637, (Feb. 17, 1984), 701-703.
B. Boboye, "Degradation of Trehalose by Rhizobia and Characteristics of a Trehalose-Degrading Enzyme Isolated from *Rhizobium* Species NGR234," Journal of Applied Microbiology (2004), 97: 256-261.
Maurice, et al., "Survival and Change in Physiological State of *Bradyrhizobium japonicum* in Soybean (*Glycine max* L. Merril) Liquid Inoculants After Long-Term Storage," World Journal of Microbiology & Biotechnology (2001), 17: 635-643.
Mary, et al., "Production and Survival During Storage of Spray-Dried *Bradyrhizobium japonicum* Cell Concentrates," Journal of Applied Bacteriology (1993), 74: 340-344.
Obaton, et al., "Are *Bradyrhizobium japonicum* Stable During a Long Stay in Soil?" Plant and Soil (2002), 245: 315-326.
Cliquet, et al., "Influence of Culture Medium and Growth Stage on the Survival of *Bradyrhizabium japonicum* During Desiccation and Storage at Two Relative Humidities," Symbiosis (1994), 16: 279-287.
Mary, et al., "Differences Among *Rhizobium meliloti* and *Bradyrhizobium japonicum* Strains in Tolerance to Desiccation and Storage at Different Relative Humidities," Soil Biol. Biochem. vol. 26, No. 9 (1994), 1125-1132.
Ping Xie, et al., "Accumulation of Soluble Carbohydrates, Trehalase and Sucrose Synthase in Effective (Fix+) and Ineffective (Fix−) Nodules of Soybean Cultivars that Differentially Nodulate with *Bradyrhizobium japonicum*," Functional Plant Biology (2003), 30: 965-971.
Mashhady, et al., "Effect of Salinity on Survival and Symbiotic Performance Between *Rhizobium meliloti* and *Medicago sativa* L. in Saudi Arabian Soils," Arid Soil Research and Rehabilitation (1998), 12: 3-14.

(Continued)

*Primary Examiner* — Susan McCormick Ewoldt
(74) *Attorney, Agent, or Firm* — Drinker Biddle & Realth LLP

(57) ABSTRACT

The present invention includes a method for producing a liquid inoculant containing a desiccant. The method can improve survival and stability of bacteria in liquid inoculants in pack and on seeds. The method includes providing a liquid inoculant of a bacterium grown to a substantially stationary phase. A desiccant treatment containing a desiccant is added to the liquid inoculant to form a partially desiccated inoculant product. The partially desiccated inoculant product can be packaged and stored. The partially desiccated inoculant product can also be applied to seeds.

29 Claims, 14 Drawing Sheets

OTHER PUBLICATIONS

Ghittoni, et al., "Peanut Rhizobia Under Salt Stress: Role of Trehalose Accumulation in Strain ATCC 51466," Can. J. Microbiol (1995), 41: 1021-1030.

Sussich, et al., "Reversible Dehydration of Trehalose and Anhydrobiosis: From Solution State to an Exotic Crystal?," Carbohydrate Research (2001), 334: 165-176.

Thorne, et al., "Cell Density-Dependent Starvation Survival of *Rhizobium leguminosarum* bv. Phaseoli: Identification of the Role of an N-Acyl Homoserine Lactone in Adaptation to Stationary-Phase Survival," Journal of Bacteriology, Feb. 1999, 981-990.

Zayed, et al., "Influence of Trehalose and Moisture Content on Survival of *Lactobacillus salivarius* Subjected to Freeze-Drying and Storage," Process Biochemistry (2004), 39: 1081-1086.

Leslie, et al., "Trehalose and Sucrose Protect Both Membranes and Proteins in Intact Bacteria During Drying," Applied and Environmental Microbiology, Oct. 1995, 3592-3597.

Athar, et al., "Effect of Drought on the Growth and Survival of *Rhizobium meliloti* Strains from Pakistan and Nepal, " Journal of Arid Environments (1997), 35:335-340.

Müller, et al., "Trehalose Affects Sucrose Synthase and Invertase Activities in Soybean (*Glycine max* [L.] Merr.) Roots," Journal of Plant Physiology (1998), 153: 255-257.

Maruta, et al. "Cloning and Sequencing of Trehalose Biosynthesis Genes from *Rhizobium* sp. M-11," Biosci. Biotech. Biochem. (1996), 60(4): 717-720.

Thorne, et al., "Adaptation to Nutrient Starvation in *Rhizobium leguminosarum* bv. Phaseoli: Analysis of Survival, Stress Resistance, and Changes in Macromolecular Syntheses During Entry To and Exit from Stationary Phase," Journal of Bacteriology, Nov. 1997, 6894-6901.

Souzu, "Basic Aspects and Industrial Strategies for the Preservation of Microorganism by Freezing and Drying" 1997.

Temprano, et al., "Survival of Several *Rhizobium/Bradyrhizobium* Strains on Different Inoculant Formulations and Inoculated Seeds," Int. Microbiol (2002), 5: 81-86.

J. Mugnier and G. Jung "Survival of Bacteria and Fungi in Relation to Water Activity and the Solvent Properties of Water in Biopolymer Gels," *Applied and Environmental Microbiology*, Jul. 1985, p. 108-114, vol. 50. 1.

Roughley, R.J. "The Preparation and Use of Legume Seed Inoculants," Plant and Soil, 32, 675-701 (1970).

* cited by examiner

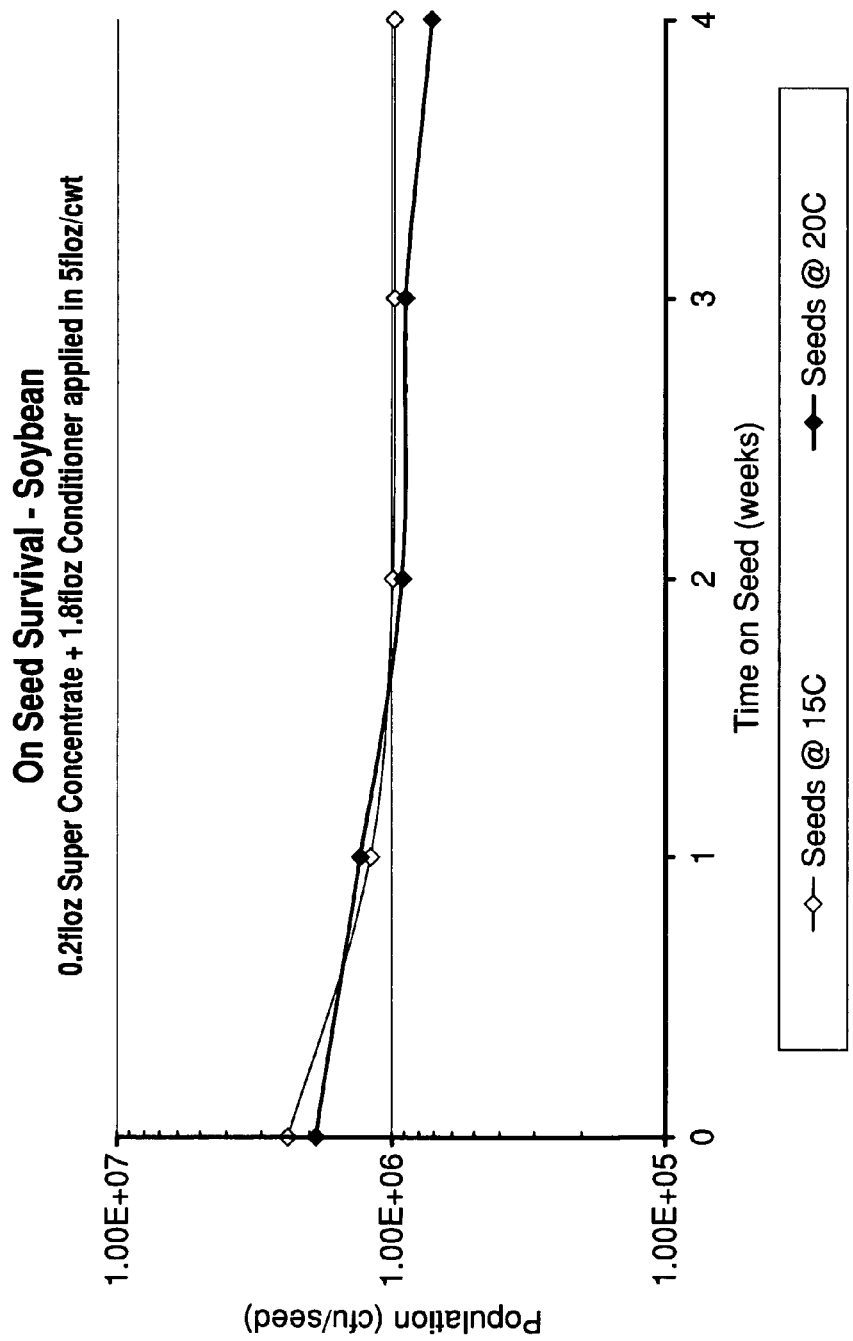

ENHANCED SHELF LIFE AND ON SEED STABILIZATION OF LIQUID BACTERIUM INOCULANTS

PRIOR APPLICATIONS

This is a Continuation in Part application of patent application Ser. No. 11/020,714, filed Dec. 23, 2004, the entire disclosure of which is incorporated herein by reference.

TECHNICAL FIELD

The invention relates to liquid inoculants. Particularly, the invention relates to a method for improving survival and stability of bacteria of liquid inoculants in pack and when applied to seeds.

BACKGROUND OF THE INVENTION

Various microorganisms are known to have a beneficial effect on plants. These microorganisms include bacteria of the genera *Rhizobium, Bradyrhizobium, Sinorhizobium, Mesorhizobium, Pseudomonas, Serratia, Bacillus, Paenibacillus, Pasteuria, Azotobacter, Enterobacter, Azospirillum, Methylobacterium, Cyanobacteria* (blue-green algae), and mycorrhizal fungae. Such microorganisms can be introduced to the plants by the use of inoculant compositions. The process by which inoculant compositions are created includes the step of fermenting the microorganisms, generally on a nutrient media.

The inoculant compositions can be applied directly onto seeds of plants or can be applied in furrow immediately prior to the seeds being planted. Inoculation of the seeds or soil with beneficial microorganisms for crop improvement has been practiced for a number of years. However, variable and inconsistent results have often been observed, possibly due to loss of inoculant viability or variability of dosage due to changes in inoculant viability.

When an inoculant is applied at the time of sowing, whether in furrow application or by on-seed application, the microorganisms in the inoculant do not have time to adjust to the new environment. Consequently, the microorganisms in the inoculant may have a low rate of survival.

Currently, to improve viability of the microorganisms in the inoculant, extenders based on sugars or polymers are added when the inoculant is added to the seed, or at the time of sowing. Because the extenders are added after packaging of the inoculant, the extenders have no effect on the survival and stability of the inoculant in pack.

Also, the addition of extenders at the time the inoculant is added to the seed or at the time of sowing is cumbersome and generally must be performed by the end-users of the inoculant (e.g., farmers) in a non-controlled environment (e.g., in a barn or in a farm field). Thus, there is an increased likelihood that the extenders will be improperly applied.

To overcome the problems associated with adding extenders after the inoculant is prepared, extenders have also been added to the nutrient medium prior to the fermentation step of creating the liquid inoculant. However, addition of the extenders, at an optimal level for on-seed survival, before fermentation inhibits growth of the microorganisms.

Therefore, there is a need for a method for increasing survival and stability of a microorganism (e.g., bacteria) of a liquid inoculant during storage, and for improving on-seed survival and stability of a microorganism of a liquid inoculant once placed on a seed.

SUMMARY OF THE INVENTION

One embodiment of the present invention is a method for preparing a liquid inoculant product containing a desiccant. The method includes providing a liquid inoculant of a bacterium grown to a substantially stationary phase. A desiccant treatment comprising a desiccant is added to the liquid inoculant to form a partially desiccated inoculant product.

In another embodiment of the present invention, the partially desiccated inoculant product is packaged and stored.

In a further embodiment of the present invention, the partially desiccated inoculant is applied to a seed.

BRIEF DESCRIPTION OF THE DRAWINGS

FIG. 14 is a graph of *Bradyrhizobium* population, as function of time, resulting from the practice of several embodiments of the present invention.

DETAILED DESCRIPTION OF THE DRAWINGS

Figure 1:
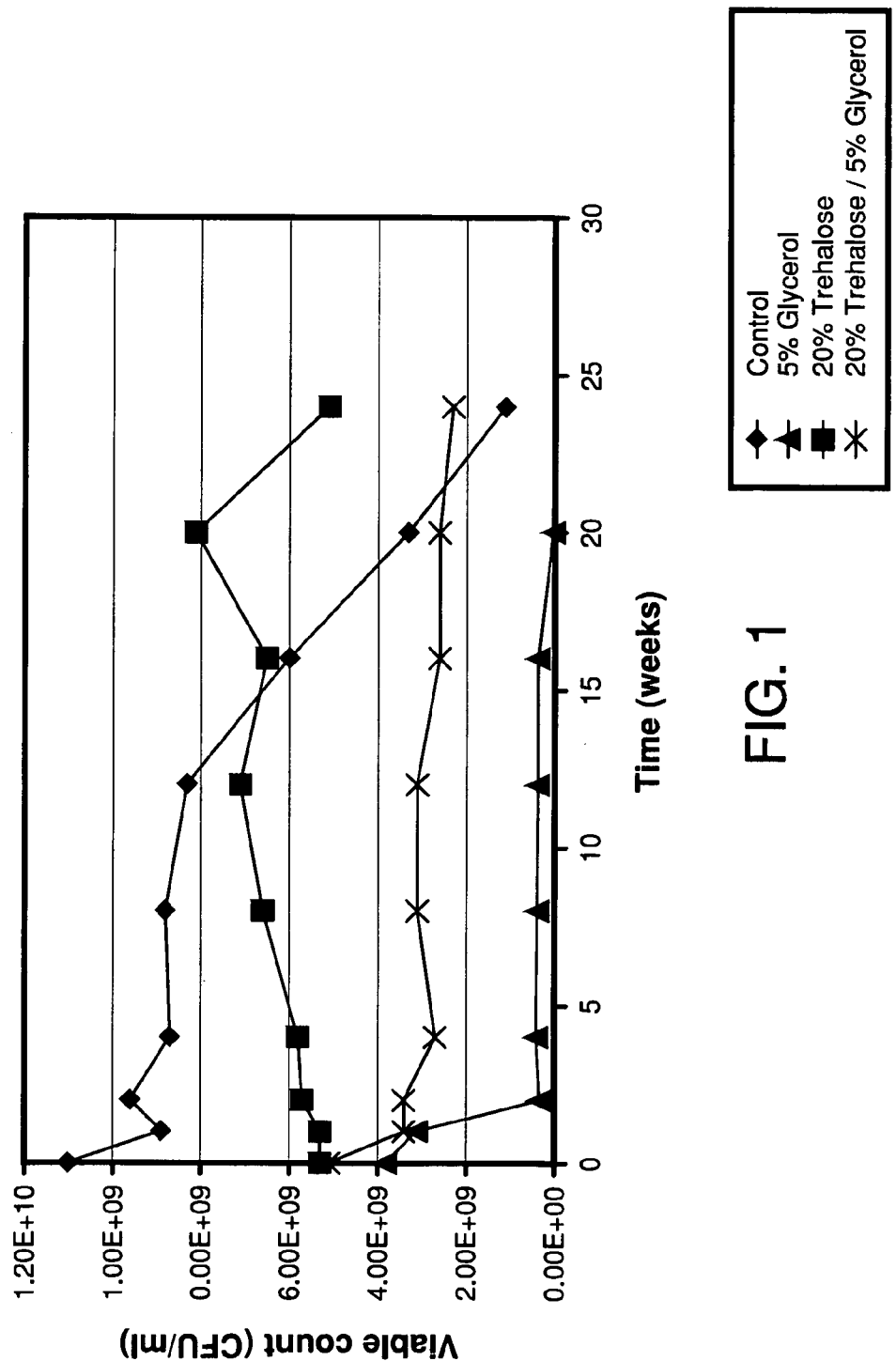
FIG. 1 is a graph of *Bradyrhizobium japonicum* ("*B japonicum*") survival in a liquid broth, as a function of time and temperature, resulting from the practice of several embodiments of the present invention.

A method for preparing a liquid inoculant of a bacterium is provided. The method includes the addition of a desiccant to the liquid inoculant after the bacteria have been grown to a substantially stationary phase. The addition of the desiccant to the inoculant forms a partially desiccated inoculant product.

The method can provide for increased stability of the bacteria when the partially desiccated inoculant product is "in pack" (i.e., contained in a package) and when the partially desiccated inoculant product is applied onto a seed. The increased stability can result in enhanced survival of the bacteria both in pack and on seed.

Bacteria are introduced to a liquid nutrient media to create a bacterial culture. Various bacteria, including but not limited to bacteria of the genera *Rhizobium Bradyrhizobium, Sinorhizobium, Mesorhizobium, Pseudomonas, Serratia, Bacillus, Paenibacillus, Pasteuria, Azotobacter, Enterobacter, Azospirillum, Methylobacterium, Cyanobacteria* (blue-green algae), can be introduced to the liquid nutrient media. Other microorganisms (e.g., mycorrhizal fungy, which, as used herein, is included in the definition of the term "bacteria") can be introduced to the liquid nutrient media to create the bacterial culture. For *Rhizobium* and *Bradyrhizobium*, preferred strains include *Bradyrhizobium japonicum, Rhizobium meliloti, Rhizobium leguminosarum* biovar *trifolii, Rhizobium leguminosarum* biovar *viceae* and *Rhizobium leguminosarum* biovar *phaseoli*. These bacteria are capable of forming nodules in the roots of species of leguminous plants. Although the following description is mainly directed to *Rhizobium* inoculant compositions, it will be appreciated that similar principles apply to the use of other microorganisms.

The liquid nutrient media into which the bacteria are introduced can be any liquid nutrient media known to those skilled in the art to be compatible with the bacteria chosen. For example, YMB is a commonly used medium for *Rhizobium*. The composition of YMB is presented in Table 1.

TABLE 1

Characteristics of YMB

| Yeast Extract | 0.50 g/L |
|---|---|
| Mannitol | 10.0 g/L |
| K2HPO4 | 0.50 g/L |
| MgSO4•7H2O | 0.2 g/L |
| NaCl | 0.1 g/L |
| Water | 1 L |
| pH | 6.8 |

After the bacteria is added to the liquid nutrient media, the bacterial culture can then be incubated (or fermented) to allow the bacteria to grow to a "substantially stationary phase". The "substantially stationary phase" is defined to include the culture period from late "log phase" to "stationary phase". The "log phase" is defined as the phase that occurs after the lag phase at the beginning of fermentation and as the phase where nutrients are generally unlimited and where there is generally exponential growth of the bacteria. The "stationary phase" is defined as the phase that occurs after the log phase and as the phase in which bacterial growth has essentially ceased. The stationary phase is generally reached when the liquid nutrient media is substantially exhausted. As used herein, the substance containing the bacteria that is incubated to the substantially stationary phase is termed a "liquid inoculant".

Generally, the bacteria incubation period can be between 1 and 15 days. More specifically, the incubation period can be between 2 and 7 days. During the incubation period the liquid nutrient media and bacteria can be aerated and maintained at a temperature suitable for growth. Aeration can be performed through the use of a shaking incubator, a fermentation reactor, or other similar means. The precise conditions for incubation depend on the type of bacteria and the type of liquid nutrient media used. For example, *B japonicum* can be incubated on a nutrient media in a shaking incubator for about 1-10 days at temperatures from about 20° C. to about 35° C. Preferably, *B japonicum* is incubated for about 2-7 days at about 28° C. to allow the bacteria to grow.

The bacteria count at the substantially stationary phase varies depending on the bacteria. For example, for *Rhizobium* bacteria, bacteria counts in the liquid inoculant from about $1 \times 10^9$/ml to about $5 \times 10^{11}$/ml are contemplated. In that example, the liquid inoculant can comprise about $1 \times 10^{10}$ bacteria counts per ml. These are exemplary amounts, and as such other amounts are contemplated to be within the scope of the present invention.

After the substantially stationary phase is attained (i.e., after the bacteria has been allowed to grow at an exponential rate rate), a desiccant treatment containing a desiccant is introduced into the liquid inoculant to create a partially desiccated inoculant product. The term "desiccant treatment" means a mixture of a desiccant and a diluting substance, generally water. The term "desiccant" means a substance that, when added to water, reduces water activity (which is defined as the partial pressure of water vapour at the surface of the substance divided by saturation pressure). Reduction of water activity to a level less than 0.995 is contemplated to be effective in enhancing in pack survival of the bacteria in the partially desiccated inoculant product. Reduction of water activity to a level less than 0.990, preferably less than about 0.980, is contemplated to be effective in enhancing on seed survival of the bacteria in the partially desiccated inoculant product.

As used herein, "desiccants" can include any compound or mixture of compounds that can be classified as a desiccant regardless of whether the compound or compounds are used in such concentrations that they in fact have a desiccating effect on the liquid inoculant. Examples of suitable desiccants include one or more of trehalose, sucrose, glycerol, and triethylene glycol. Other suitable desiccants include, but are not limited to, non reducing sugars and sugar alcohols (e.g., mannitol, sorbitol).

The amount of desiccant introduced into the liquid inoculant generally is in a concentration from about 5% to about 50% by weight/volume of the partially desiccated inoculant product. When the desiccant is trehalose, the desiccant is preferably in a concentration from about 10% to about 40% by weight/volume of the partially desiccated inoculant product. More preferably, the trehalose is in a concentration from about 20% to about 30% by weight/volume of the partially desiccated inoculant product. When the desiccant is sorbitol, the desiccant is preferably in a concentration from about 10% to about 35% by weight/volume of the partially desiccated inoculant product. More preferably, the sorbitol is in a concentration from about 15% to about 20% by weight/volume of the partially desiccated inoculant product.

The desiccant treatment can include a mixture of more than one desiccant. In fact, the mixtures can be any combination of two or more desiccants, as desiccant is defined herein. For example, the desiccant treatment can include a mixture of trehalose and glycerol, a mixture of trehalose and sucrose, or a mixture of sucrose and triethylene glycol. A mixture of trehalose and glycerol can include trehalose in concentrations from about 5% to about 40% by weight/volume of the partially desiccated inoculant product and glycerol in concentrations from about 1% to about 10% by weight/volume of the partially desiccated inoculant product. More particularly, the concentrations of the trehalose and the glycerol in the mixture can be about 20% and about 5% by weight/volume of the partially desiccated inoculant product, respectively. Desiccant treatments that include trehalose as a desiccant have been found to be particularly beneficial in the present invention with on seed survival of bacteria typically used on soybeans (e.g., *B japonicum*).

Other mixtures are also contemplated. For example, sorbitol can be combined with other desiccants such as trehalose and sucrose. Sorbitol can also be combined with polymers such as polyvinylpyrrolidone ("PVP"). Desiccant treatments that include sorbitol as a desiccant have been found to be particularly beneficial in the present invention with on seed survival of bacteria typically used on pea and lentils (e.g., *Rhizobium leguminosarum* biovar *viceae*). The beneficial effect of the sorbitol is contemplated to occur regardless of whether the combination is applied to pea and lentils or applied some other crop such as corn.

The desiccant treatment can be added to the liquid inoculant while the liquid inoculant is still in the vessel used during incubation (e.g., fermentation reactor or shaking incubator). Alternatively, the desiccant treatment can be added to the liquid inoculant during packaging.

When the desiccant treatment is added to the liquid inoculant prior to the packaging step (e.g., while the liquid inoculant is still in the incubation vessel), the partially desiccated inoculant is preferably allowed to enter a conditioning phase once the desiccant treatment is added to the liquid inoculant. The conditioning phase includes allowing the partially desiccated inoculant product to breathe, i.e., be exposed to ambient air. During the conditioning phase the bacteria are preferably metabolizing at or near a full rate. A significant benefit of the conditioning phase is that the bacteria are allowed to adapt to the desiccant. Without the conditioning phase, the desiccant could shock the bacteria, resulting in reduced bacteria survival.

Preferably, the conditioning phase is about 1 to about 10 days. More preferably, the conditioning phase is about 2 to about 3 days. The length of time for the conditioning phase can vary depending on the type of desiccant added, the type of bacteria in the inoculant, and so on.

In one embodiment, sufficient desiccant is present to at least partially desiccate the bacteria in the partially desiccated inoculant product, thereby: (1) improving the stability and survival of the bacteria in subsequent steps such as packaging and storing, (2) and improving the stability and survival of the bacteria in subsequent steps such as on-seed application of the partially desiccated inoculant product.

The partially desiccated inoculant product can then be packaged and stored. The packaging can be any standard packaging known in the industry. For example, the partially desiccated inoculant product can be packaged in polyethylene bladders.

After packaging the partially desiccated inoculant product can be stored. The storage conditions can include refrigerated to ambient temperatures and low to moderate relative humidity. Preferably, storage conditions include a temperature below about 35° C. and a relative humidity below about 80%. More preferably, the storage conditions include a temperature of about 4° C. to about 5° C., with a maximum preferred temperature of about 15° C.

The partially desiccated inoculant product can be applied to a variety of seeds. For example, the partially desiccated inoculant product can be applied to seeds for leguminous plants and non-leguminous plants. Leguminous plants form a large group of plants including vegetables of economic importance such as soybean, lucerne (alfalfa), peanut, peas, lentils, beans, and the like. Non-leguminous plants include corn and the like. The bacteria of the partially desiccated inoculant product can colonize the rhizosphere and/or infect the roots of the plants, as they permeate into the radicular hairs and colonize the root, producing nodules. As a result of this symbiotic relation, plants can turn gaseous nitrogen into organic compounds of nitrogen through nitrogen fixation. The plants then can use these organic compounds to grow.

The number of bacteria on a seed at the time the partially desiccated inoculant product is applied to the seed varies. The number of bacteria on the seed 10 weeks after the partially desiccated inoculant product is applied can also vary, but it is contemplated that the number should not represent a significant departure from the original amount. In other words, there should not be a sharp decline in bacteria count/seed over time. For example, if the number of bacteria on a seed is at least $6 \times 10^5$ at the time the partially desiccated inoculant product is applied to the seed, the number of bacteria on the seed after about 10 weeks is preferably at least $1 \times 10^5$.

An advantage of inoculants prepared according to the present invention is that the inoculants can be applied at rates lower than what has heretofore been practiced (i.e., less than about 4.2 fluid ounces/cwt), while at the same time achieving on-seed survival of the bacteria that meet or exceed survival rates that have previously been achieved (i.e., greater than $10^5$ cfu/seed after 12 weeks on seed). Such low volume rate application with high on-seed survival is advantageous for several reasons.

First, low volume application rates translate into reduced manufacturing and transportation costs (i.e., less volume to manufacture and transport for effectively the same yield).

Second, low volume application rates prevent seed bridging (i.e., the clumping of two or more seeds because of excess liquid volume). The threshold for seed bridging is generally about 5 fluid ounces/hundred pounds of seed ("cwt"), with high levels of seed bridging occurring above about 6 fluid ounces/cwt. Seed bridging inhibits full coverage of the seed with the inoculant and also inhibits even distribution of the seeds during planting.

Third, low volume application of inoculants allows for concurrent application of various functional materials while maintaining high on-seed survival of the bacteria but without exceeding the seed bridging threshold (i.e., typically greater than about 6 fluid ounces per 100 pounds). The functional materials can include cidal compounds. The cidal compounds can include insecticides, fungicides, herbicides, bactericides, pesticides, virucides, acaracides, miticides, nematicides, rodenticides, or combinations thereof. Preferred cidal compounds include fungicides and insecticides. For example, APRONMAXX RFC (Mefenoxam, Fludioxonil), APRONMAXX RTA (Mefenoxam, Fludioxonil), WARDEN RTA (Mefenoxam, Fludioxonil), CRUISERMAXX (PAK) (Thiamethoxam, Mefenoxam, Fludioxonil), CRUISER (Thiamethoxam), and BEAN PAK (Mefenoxam, Fludioxonil) are particularly preferred.

The cidal compounds can be combined with an inoculant of the present invention in any number of ways to form an inoculant mixture. For example, for 100 pounds of seed, 2 fluid ounces of an inoculant prepared according to the present invention, 1 fluid ounce of a first cidal compound, 1 fluid ounce of a second cidal compound, and 1 fluid ounce of water can be applied onto the seed as a mixture. Such an inoculant mixture would have the benefit of high on-seed survival, the benefit of the first cidal compound, and the benefit of the second cidal compound without the detriment of seed bridging and without requiring a new formulation to achieve the benefits and avoid the detriments. If desired, the inoculant mixture can include water at volumes higher than 1 fluid ounce. Increased water volumes allow for increased seed coverage and also extend on-seed shelf life of the inoculant mixture.

The timing of the combination of a cidal compound and an inoculant of the present invention can also vary. The cidal compound and the inoculant can be mixed together to form a mixture and then that mixture is applied to the seeds. The cidal compound and the inoculant can be concurrently applied to the seeds. The cidal compound and the inoculant can be applied sequentially to the seeds, with the order and timing of application being variable.

For seeds having a size from about 2,000 to 5,000 seeds per pound (e.g., soybeans and peas), the total volume of liquids in an inoculant mixture (e.g., inoculant only, inoculant plus water, inoculant plus cidal compound, inoculant plus cidal compound plus water) applied to those seeds is preferably greater than about 4.0 fluid ounces/cwt. Smaller sized seeds (i.e., greater than about 5,000 seeds per pound) have an increased surface area. Consequently, to achieve a desired on seed stability of the bacteria (e.g., greater than $10^5$ cfu/seed after about 10 weeks on seed), higher total volume of liquids in the inoculant mixture may be necessary. Conversely, for larger sized seeds, lower total volume of liquids in the inoculant mixture may be necessary to achieve the desired on-seed stability of the bacteria.

Examples 4 and 5 show the on seed survival of bacteria when the partially desiccated inoculant of the present invention is applied at a low volume application rate.

Preferably, the inoculant is packaged individually in bladders. The bladders can be made from polypropylene, polyethylene and other similar materials. Alternatively, the inoculant can be packaged with one or more cidal compounds, and/or one or more other ingredients such as colorants and *Bacillus subtilis*. The combination inoculant/cidal compound(s), inoculant/other ingredient(s), inoculant/cidal compound(s)/other ingredient(s) can be packaged together as multi-packs (e.g., twin packs).

In a further alternative, the inoculant can be packaged as two separate components. The first component is a "super concentrate". The super concentrate includes bacteria, water, at least one desiccant, and at least one polymer. The super concentrate can also include a gelling agent. The bacteria can be any of the bacteria discussed herein, but is preferably *B. japonicum*. The desiccant can be any of the desiccants discussed herein, but is preferably trehalose. The polymer can be any of the polymers discussed herein, but is preferably vinyl pyrrolidone and vinyl acetate copolymers. The gelling agent can be any of the gelling agents discussed herein, but is preferably gellan gum.

The second component is a "conditioner". The conditioner includes water, at least one desiccant and at least one polymer. The conditioner can also include water. The desiccant can be any of the desiccants discussed herein, but is preferably trehalose. The polymer can be any of the polymers discussed herein, but is preferably vinyl pyrrolidone and vinyl acetate copolymers.

To create a super concentrate, bacteria can be cultured in a nutrient medium for about 2 to about 10 days at a temperature of about 20° C. to about 35° C. The nutrient medium can be micro-filtered to a smaller volume (e.g., from 100 liters to 5 liters). To micro-filter the nutrient medium, the medium is repeatedly passed through a sterilized micro-filtration unit until a desired level of concentration of bacteria is reached (e.g., about $1 \times 10^{11}$ cfu/ml to about $1 \times 10^{12}$ cfu/ml). The micro-filtered volume can then be made up to a higher volume unit that is less than the original volume of the nutrient medium (e.g., from 5 liters to 10 liters) by the addition of water, a desiccant, a polymer, and possibly a gelling agent (e.g., water+30% w/v (based on final volume), 1% w/v vinyl pyrrolidone and vinyl acetate copolymer, and 0.05% w/v gellan gum). The resulting unit can be stored at about 2° C. to about 20° C. prior to on seed application.

To create a conditioner, a mixture of a desiccant, a polymer and possibly water can be prepared separate from the super concentrate (e.g., 90 liters of trehalose (30% w/v), vinyl pyrrolidone and vinyl acetate copolymer (1%), and gellan gum (0.05% w/v)). The mixture can be sterilized (but does not necessarily have to be), aseptically packaged and then stored at about 15° C. to about 25° C. prior to on seed application.

The super concentrate and the conditioner can be applied together onto seeds. The combination can be applied with water and/or a functional compound (e.g., a cidal compound). For application to 100 pounds of seed, the amount of super concentrate is preferably from about 0.1 fl oz. to about 0.5 fl oz., and is more preferably about 0.2 fl oz. The amount of conditioner is preferably about 1.2 fl oz. to about 2.5 fl oz., and is more preferably about 1.8 fl oz. The amount water and/or functional compound is preferably about 1.5 fl oz. to about 5.5 fl oz., and is more preferably about 3.0 fl oz. The concentration of bacteria in the combined super concentrate and conditioner is preferably about $1 \times 10^9$ cfu/ml to about $5 \times 10^{11}$ cfu/ml, and is more preferably about $1 \times 10^{10}$ cfu/ml.

To improve stability and survival of the bacteria in the partially desiccated inoculant product in pack and on seeds, it is contemplated that a polymer can be optionally added to the partially desiccated inoculant product prior to applying the partially desiccated inoculant product to the seed. The polymer can be added before the packaging step or after the storing step. The polymer can include polyvinyl pyrrolidone, alkylated vinyl pyrrolidone polymers, vinyl pyrrolidone and vinyl acetate copolymers (e.g., commercially available from International Specialty Products as "S-630"), vinyl pyrrolidone and styrene copolymers, polyvinyl alcohol polymers, and other similar polymers. The polymer can be in a concentration from about 1% and 25% weight/volume of the partially desiccated inoculant product.

Although the addition of the desiccant to the liquid inoculant to create a partially desiccated inoculant product after the bacteria has reached the substantially stationary phase improves stability of bacteria without the necessity of adding an extender at the time of sowing, it does not preclude the use of an extender. In fact, it is within the scope of the present invention that extenders can be applied to seeds after the partially desiccated inoculant product has been applied to the seed. The extender can be added at the time of sowing or at the time of seed application of the partially desiccated inoculant product. The extenders can include any commonly used extenders such as those based on sugars, gums, carboxymethyl cellulose, and polymers.

The partially desiccated inoculant product can be applied to peat, clay and/or other similar dry carriers to form a dry, flowable inoculant formulation. The partially desiccated inoculant product can be applied by spraying or other known means.

The invention will now be illustrated with the following non-limiting examples.

Example 1

Evaluation of Stability of *Bradyrhizobium Japonicum* in the Presence of Trehalose and a Glycerol/Trehalose Mixture

*B japonicum* was cultured in shake flasks on a nutrient media for 7 days at 28° C. in a shaking incubator to create a 7 day old mature fermentation broth. Four treatments (see Table 2) were prepared in 250 ml shake flasks. The treatments were prepared in duplicate, so there was a total of 8×250 ml shake flasks. 50 ml of the seven day old mature fermentation broth was added to each of the shake flasks. The contents of all the flasks were allowed to equilibrate in a shaking incubator for an additional 7 days at 28° C. After equilibrium was attained, one flask from each of the treatments was transferred to static incubation at 28° C. The second flask from each of the treatments was transferred to static incubation at 35° C.

TABLE 2

Treatments - Influence of trehalose and glycerol on stability of *B japonicum*

Figure 2:
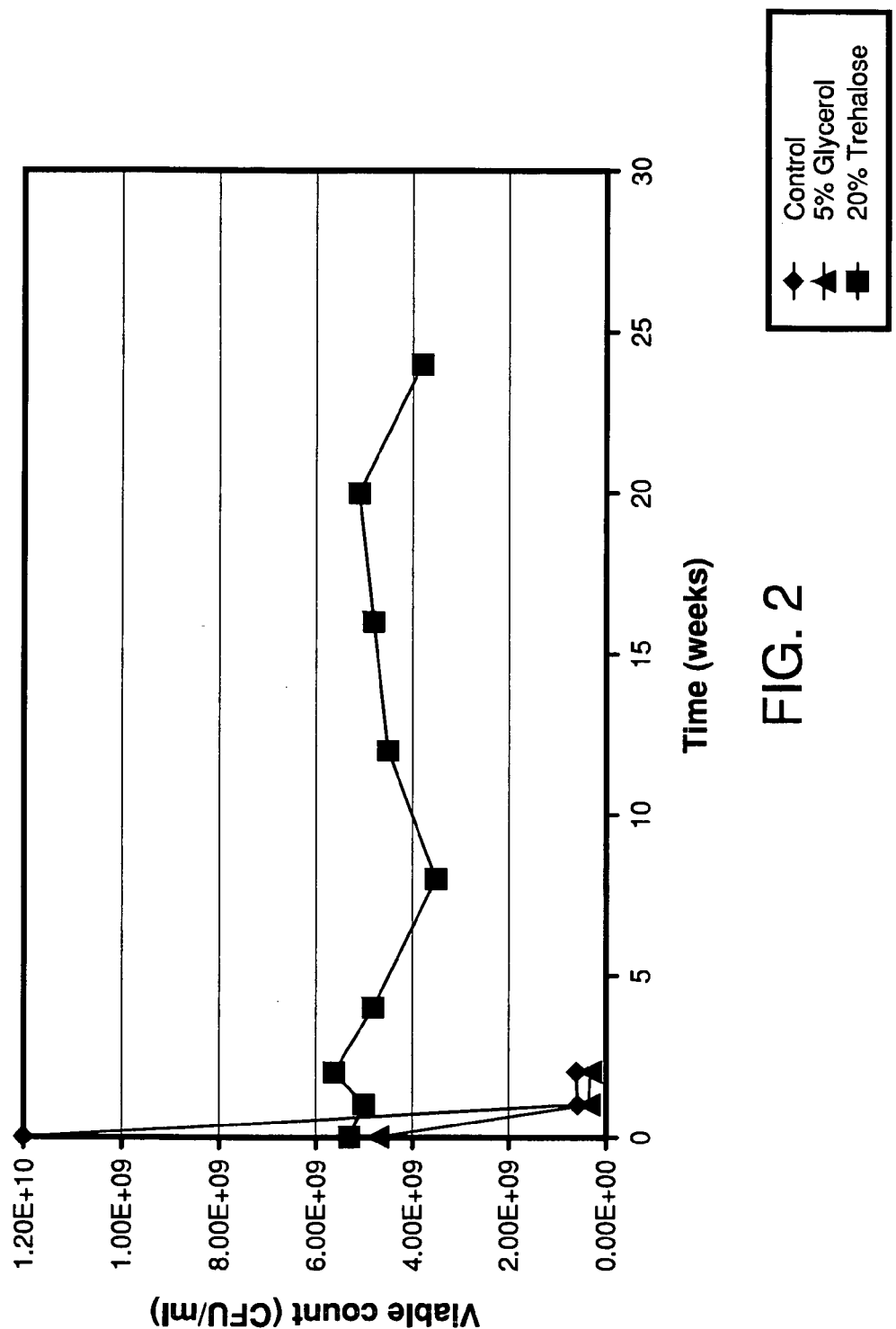
FIG. 2 is a graph of *B japonicum* survival in a liquid broth, as a function of time and temperature, resulting from the practice of several embodiments of the present invention.
Figure 3:
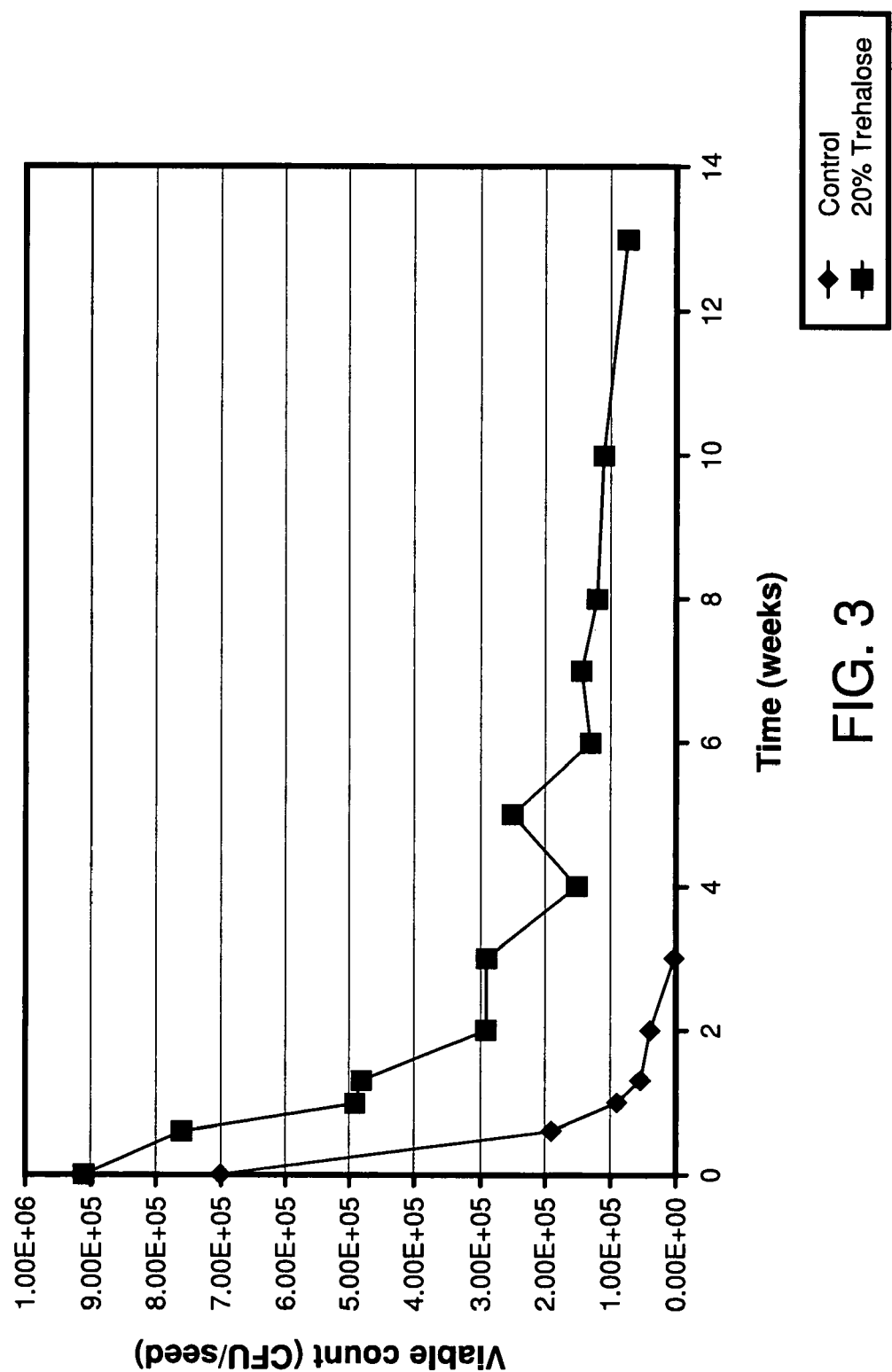
FIG. 3 is a graph of *B japonicum* survival on seed, as a function of time and temperature, resulting from the practice of several embodiments of the present invention.

| Treatments | Water(g) | Glycerol(g) | Trehalose(g) | Symbol on FIGS. 1-3 |
|---|---|---|---|---|
| Control 0% trehalose 0% glycerol | 50 | 0 | 0 | ♦ |
| 20% trehalose | 30 | 0 | 20 | ■ |
| 5% glycerol | 45 | 5 | 0 | ▲ |
| 5% glycerol + 20% trehalose | 25 | 5 | 20 | ✳ |

Samples were periodically taken from the flasks and total viable plate counts were conducted to assess the number of surviving bacteria. Plate counts were performed by first mixing the sample and then, using a calibrated pipette and sterile tip, removing 1 ml of the sample and placing it into a test tube with 9 ml of reverse osmosis (RO) water, thereby creating a $10^{-1}$ dilution. Then using a 1000 μL Rainin (calibrated and set to 1000 μL) and sterile tips, 1000 μL of the $10^{-1}$ dilution was removed from the $10^{-1}$ dilution test tube and transferred into another test tube containing 9 ml RO water, thereby creating a $10^{-2}$ dilution. These steps were then repeated up to a $10^{-7}$ dilution, noting that the test tubes containing the dilutions were vortexed and flamed between each transfer.

Using a 100 μL Rainin (calibrated and set to 30 μL) and sterile tips, 30 μL from the $10^{-1}$ dilution test tube was removed and three 10 μL drops were placed onto a nutrient agar plate, which served as a contamination detection plate. The nutrient agar was Oxoid. These steps were repeated for the other dilutions, except that for the $10^{-5}$, $10^{-6}$, and $10^{-7}$ dilutions, the samples were placed on standard plates of Congo Red Yeast Mannitol Agar ("CRYMA"-See Table 3).

TABLE 3

Composition of CRYMA Plates

| Ingredient | Amount |
|---|---|
| MgSO$_4$ | 0.204 g |
| NaCl | 0.1 g |
| K$_2$HPO$_4$ | 0.5 g |
| Yeast Extract (Difco) | 0.4 g |
| Mannitol | 10.0 g |
| Congo Red (0.25% solution) | 10 ml |
| Agar (BBL) | 15 g |

The plates were allowed to dry before inverting them and placing them into an incubator at 28° C. for 5 days. After 5 days, the number of colonies were counted under a low power microscope. The total count was calculated by taking the mean×dilution×100.

The results of the four treatments with regard to the survival of *B japonicum* incubated in a liquid broth at 28° C. are shown in FIG. 1. The results of the treatments with regard to the survival of *B japonicum* incubated in a liquid broth at 35° C. are shown in FIG. 2. The treatment with 5% glycerol became contaminated during testing and thus is not included in FIG. 2.

The results shown in FIG. 1 indicate that at 28° C., the 20% trehalose treatment and the 20% trehalose/5% glycerol treatment provide for good survivability of the bacteria in the liquid broth. The bacteria count in the control began to decrease some time between about 12 weeks and 16 weeks from the initiation of the experiment. In contrast, the bacteria count in the 20% trehalose treatment and the 20% trehalose/5% glycerol treatment remained at a relatively constant level during that same time period and even after that time period.

The results shown in FIG. 2 indicate that at 35° C., the 20% trehalose treatment provided for good survivability of the bacteria in the liquid broth. While the bacteria count of the other treatments, including the control treatment, decreased dramatically early in the experiment, the bacteria count of the 20% trehalose treatment remained relatively constant throughout the experiment.

After 10 weeks, samples were taken from the control and 20% trehalose treatment and applied to soya seeds. The seeds were incubated at 22° C. Periodically samples were taken and the number of surviving *B japonicum* was assessed. The method of assessing on-seed survival was as follows.

Soya seed lots of 500 g were weighed and placed into clean labelled resealable plastic bags. Using a 2 ml syringe or sterile 2 ml pipette, 1.38 ml of a treatment was evenly dispensed onto the seed surfaces. Ambient air was then trapped in the now seed inoculated plastic bag. The plastic bag was then immediately sealed and shaken until the seeds were evenly covered with the treatment (approximately 30 seconds). The plastic bag was unsealed and placed out of direct sunlight in ambient laboratory conditions (21° C.) until dry (approx 10 minutes). Using a dry alcohol-wiped full length scoop-spatula, exactly 100 intact seeds were randomly selected from the plastic bag. The seeds were placed into a pre-prepared 100 ml dilution bottle. The bottle was closed and then immediately shaken vigorously for approximately 1 minute. Using aseptic technique, from the prepared 100 ml bottle, serial dilutions of the suspension were prepared as follows: (1) immediately after shaking the 100 ml bottle, 1 ml of suspended bacteria and diluent was aseptically transferred into a first 9 ml dilution tube of RO water, thereby creating a $10^{-1}$ dilution (2) the $10^{-1}$ dilution was vortexed for 15 seconds, (3) immediately after vortexing, 1 ml of the $10^{-1}$ dilution was transferred into another 9 ml dilution tube of RO water to create a $10^{-2}$ dilution (4) the $10^{-2}$ dilution was then vortexed; (5) steps (3) and (4) were repeated to achieve $10^{-3}$ and $10^4$ dilutions.

Colony assessment agar plates were then labelled with the details of the dilution tube used, treatment details, and plating date. Duplicate plates were created for each dilution. Prior to taking a sample from the dilution tubes and placing them on the agar plates, the dilutions were vortexed. Then, using standard aseptic pipetting techniques, 100 μL samples of each of the dilutions were dispensed centrally onto each agar plate. Using a sterile spreader, the samples were spread evenly over the surfaces of the plates. The plates were then incubated for 7 days at 28° C. After incubation, the number of colony forming units (CFU) on each plate were counted and recorded. Then, the following calculation was used to determine the number of CFU/plate: [Mean colonies×{labelled dilution×$10^{(a)}$×$100^{(b)}$}/$100^{(c)}$], where (a) is the correction value for 0.1 ml/plate from dilution, (b) is the correction value for 100 ml in original dilution bottle, and (c) is the correction value for number of seeds in original sample.

The results of the on seed survival of *B japonicum* after 10 weeks are shown in FIG. 3. The results show that the length of time the bacteria count exceeded $1 \times 10^5$/seed was less than 1 week for the control treatment, but greater than 10 weeks for the 20% trehalose treatment. These results indicate that the treatment with trehalose concentrations at 20% provides for good survivability of the bacteria when the bacteria is placed on seeds.

Example 2

Optimization of the Level of Trehalose/Sucrose Required to Stabilize *B japonicum*

The procedure followed for the preparation of the flasks was the same as in Example 1. The treatments for this example are given in Table 4.

TABLE 4

Treatments - Influence of trehalose and sucrose on stability of *B japonicum*

| Treatment | Water(g) | Trehalose(g) | Sucrose(g) |
|---|---|---|---|
| Control | 50 | 0 | 0 |
| 5% trehalose | 45 | 5 | 0 |
| 10% trehalose | 40 | 10 | 0 |
| 20% trehalose | 30 | 20 | 0 |
| 30% trehalose | 20 | 30 | 0 |
| 40% trehalose | 10 | 40 | 0 |
| 5% sucrose | 45 | 0 | 5 |
| 10% sucrose | 40 | 0 | 10 |
| 20% sucrose | 30 | 0 | 20 |
| 30% sucrose | 20 | 0 | 30 |

Figure 4:
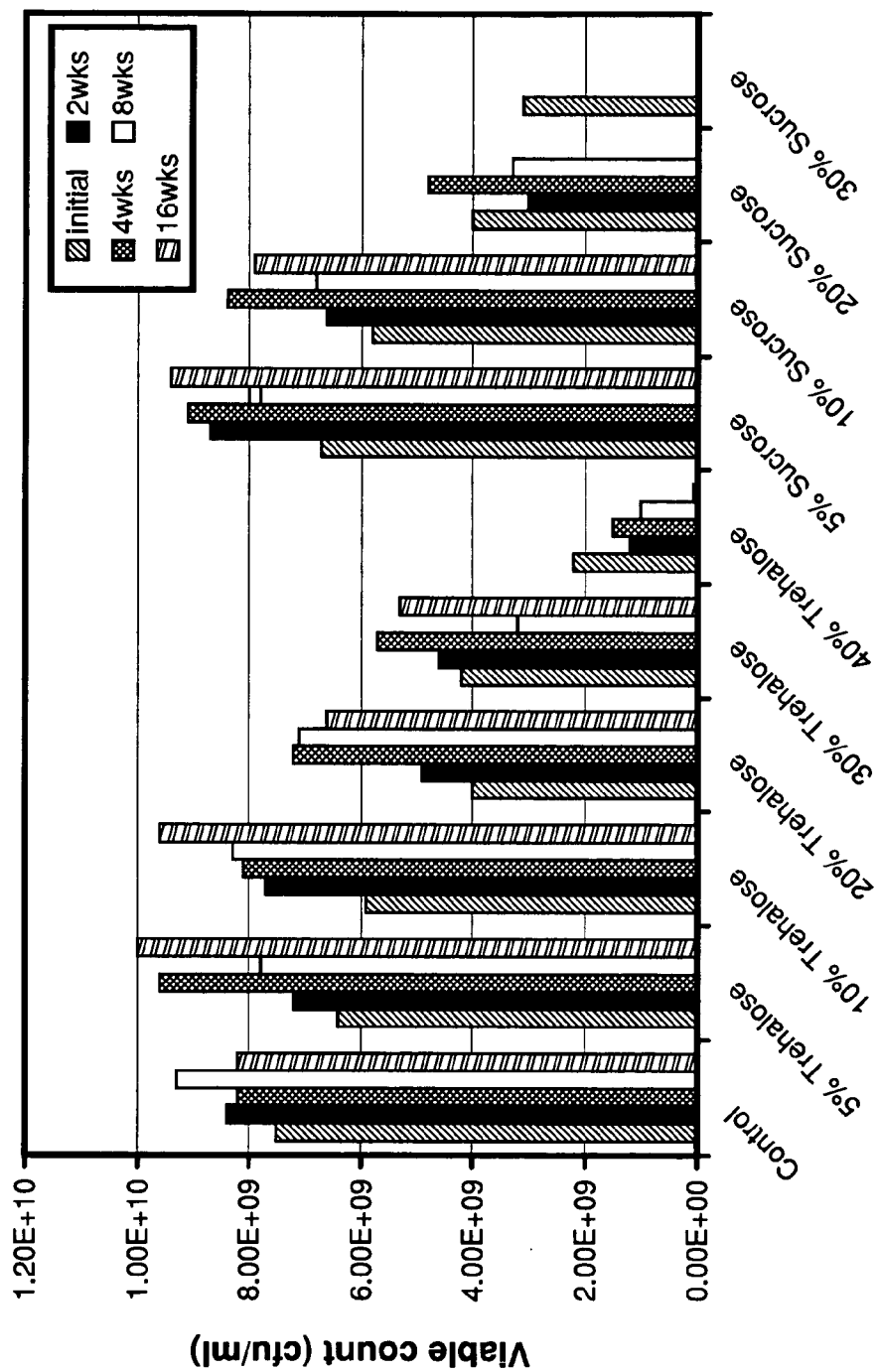
FIG. 4 is a graph of *B japonicum* survival in a liquid broth, as a function of the type and amount of desiccant, resulting from the practice of several embodiments of the present invention.

The results of the treatments with regard to the survival of *B japonicum* incubated in a liquid broth at 28° C. are shown in FIG. 4. The results of the treatments with regard to the survival of *B japonicum* incubated in a liquid broth at 35° C. are shown in FIG. 5.

The results shown in FIG. 4 indicate that at 28° C., treatments with trehalose concentrations between 10% and 30% weight/volume are optimal for survival of the bacteria in the liquid broth. FIG. 4 also indicates that treatments with sucrose concentrations between 5% and 10% weight/volume are favorable to the survival of the bacteria in the liquid broth, but not to the same extent as the trehalose treatments. FIG. 4 also indicates bacteria can survive treatments with trehalose concentrations at 40%, showing that the bacteria has to the potential to survive in a formulation that is inhibitory to growth of microorganisms.

Figure 5:
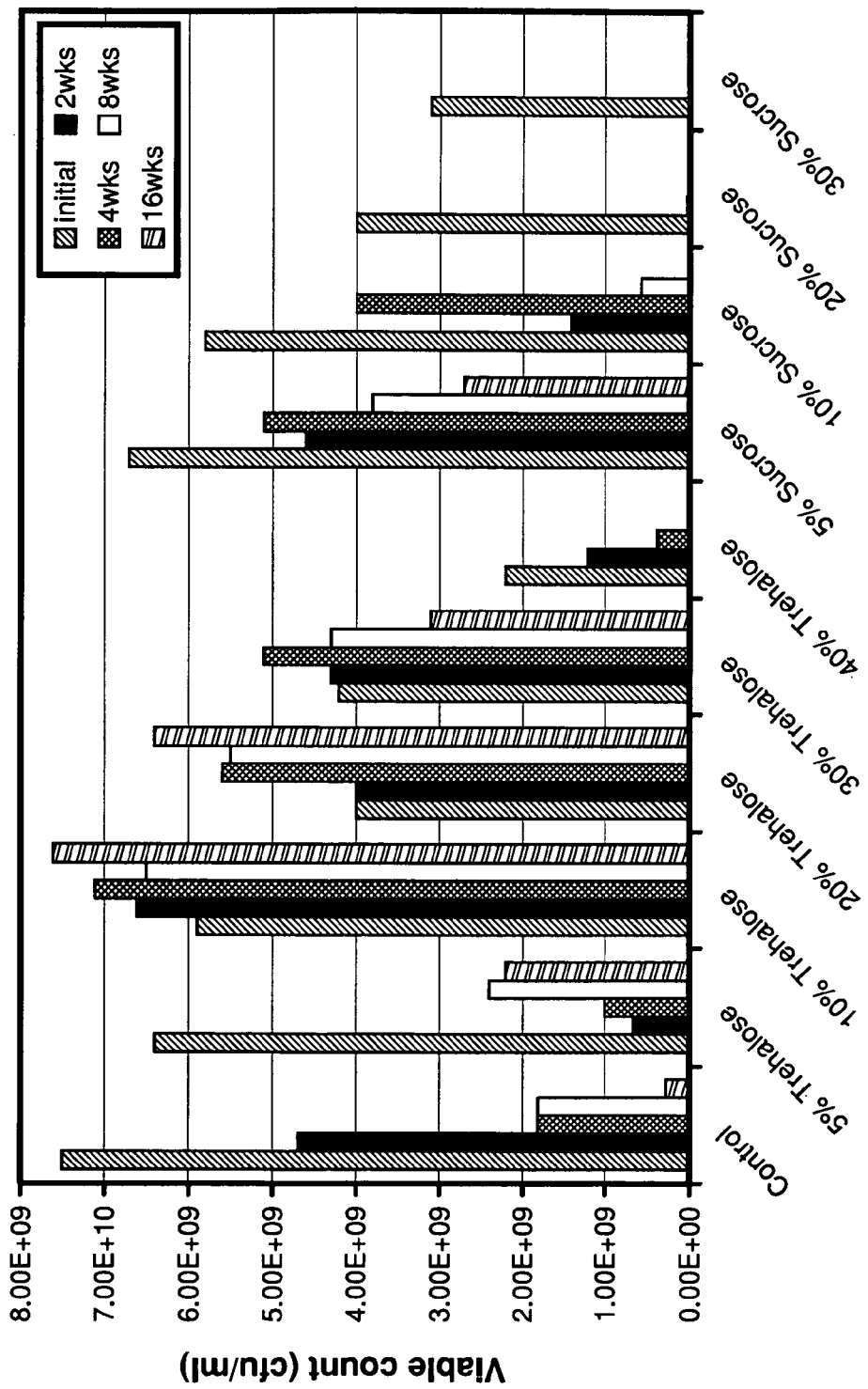
FIG. 5 is a graph of *B japonicum* survival in a liquid broth, as a function of the type and amount of desiccant, resulting from the practice of several embodiments of the present invention.

The results shown in FIG. 5 indicate that at 35° C., treatments with trehalose concentrations between 10% and 30% weight/volume are optimal for survival of the bacteria in the liquid broth. FIG. 5 also indicates that treatments with sucrose concentrations at 5% weight/volume are favorable to the survival of the bacteria in the liquid broth, but not to the same extent as the trehalose treatments.

After 10 weeks, samples were taken from the treatments listed in Table 4 and applied to soya seed. The seeds were incubated at 22° C. Samples were taken initially, after 6 days on the seed, after 2 weeks on the seed, and after 4 weeks on the seed. From these samples, the number of surviving *B japonicum* was assessed. The method of assessing on-seed survival was as described above in Example 1. The results of the on-seed survival are shown in FIG. 6.

Figure 6:
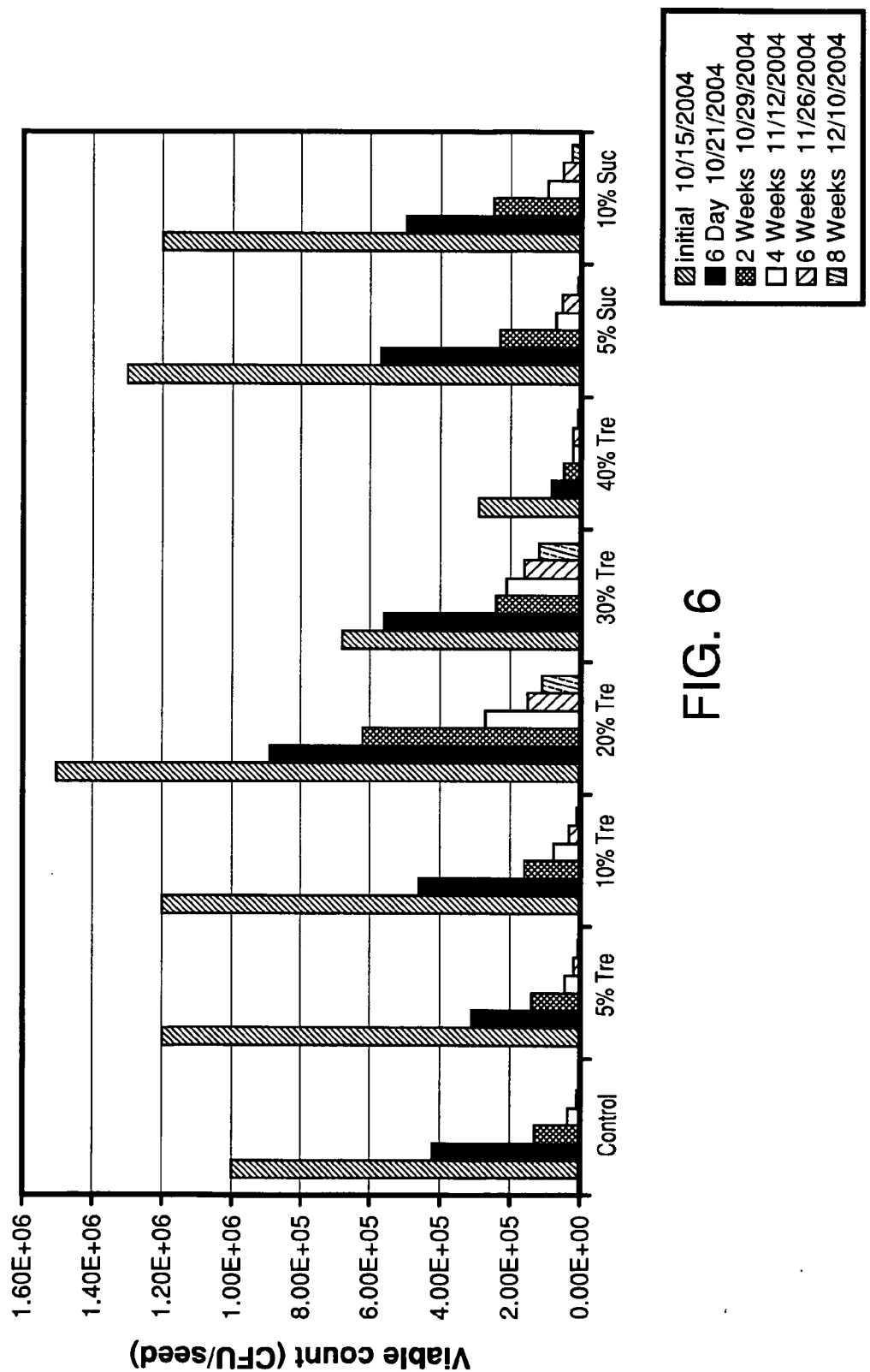
FIG. 6 is a graph of *B japonicum* survival on seed, as a function of the type and amount of desiccant, resulting from the practice of several embodiments of the present invention.

The results shown in FIG. 6 indicate that at 22° C., treatments with trehalose concentrations between 20% and 30% weight/volume are optimal for survival of the bacteria when the bacteria are placed on seeds.

Example 3

Evaluation of Stability of *Serratia proteomaculans* and *Pseudomonas fluorescens* in Liquid Broth Formulation

*Serratia proteomaculans* ("*S proteomaculans*") was cultured in a standard microbiological medium (half strength Tryptic soya broth—"TSB") for 24 hours at 22° C. to create a bacterial broth. A set of flasks was prepared, with each flask in the set corresponding to one of the treatments listed in Table 5. 50 ml of the bacterial broth was added to each of the flasks. All the flasks were allowed to equilibrate for an additional 3 days in a shaking incubator at 22° C. The flasks were then transferred to static incubation at 28° C. Periodically samples were taken and bacterial numbers were assessed by preparing serial dilutions and plating onto a half strength Tryptic soya agar—"TSA".

The same steps were repeated for *Pseudomonas fluorescens* ("*P fluorescens*").

TABLE 5

Treatments - Influence of trehalose, sucrose, and glycerol on stability of *S proteomaculans* and *P fluorescens*

| Treatment | Water(g) | Trehalose(g) | Sucrose(g) | Glycerol(g) |
|---|---|---|---|---|
| Control | 50 | 0 | 0 | 0 |
| 10% glycerol | 40 | 0 | 0 | 10 |
| 20% glycerol | 30 | 0 | 0 | 20 |
| 30% glycerol | 20 | 0 | 0 | 30 |
| 10% trehalose | 40 | 10 | 0 | 0 |
| 20% trehalose | 30 | 20 | 0 | 0 |
| 30% trehalose | 20 | 30 | 0 | 0 |
| 10% sucrose | 40 | 0 | 10 | 0 |
| 20% sucrose | 30 | 0 | 20 | 0 |
| 30% sucrose | 20 | 0 | 30 | 0 |

Figure 7:
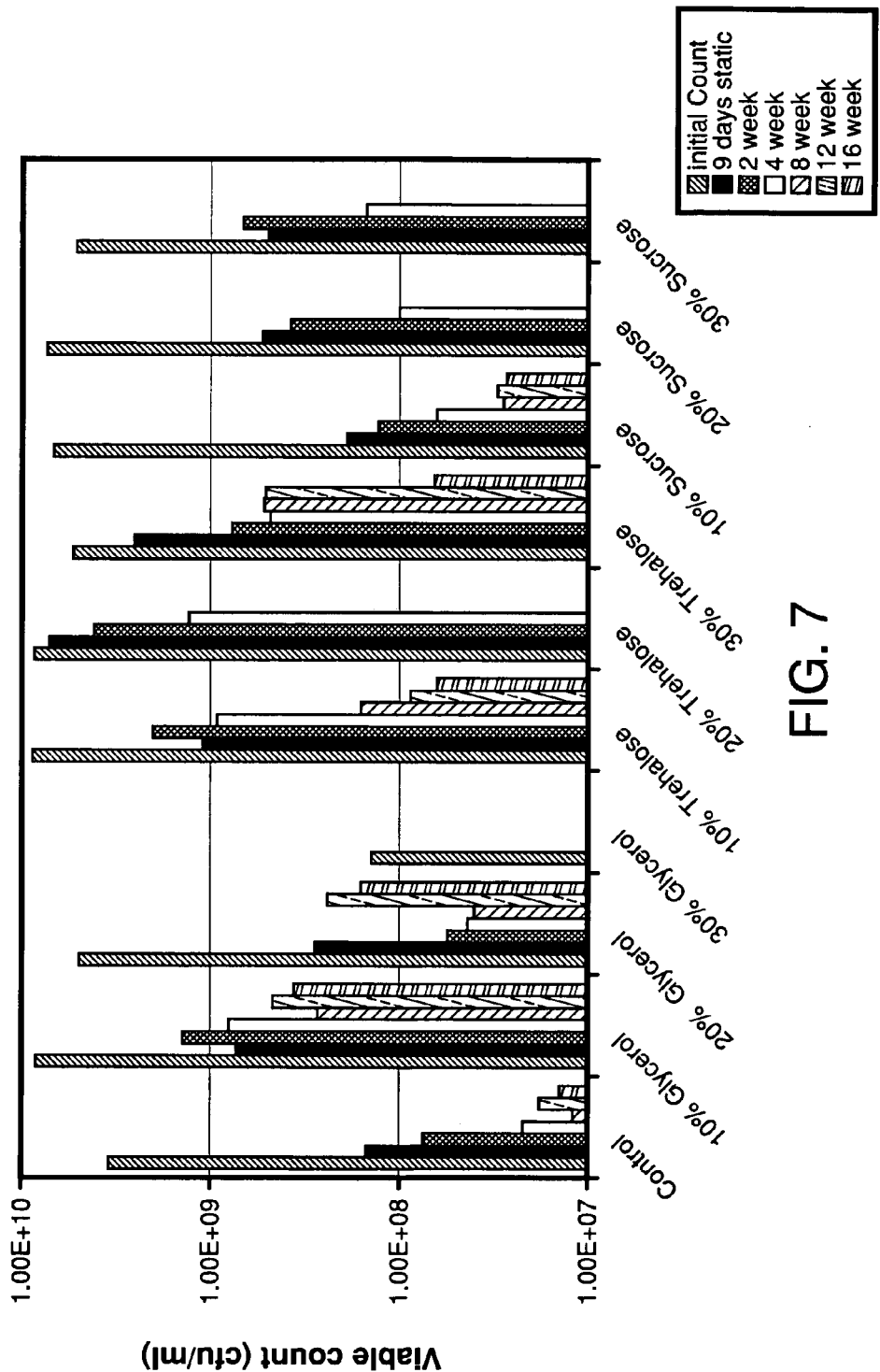
FIG. 7 is a graph of *Pseudomonas fluorescens* ("*P fluorescens*") survival in a liquid broth, as a function of the type and amount of desiccant, resulting from the practice of several embodiments of the present invention.

The results of the treatments with regard to the survival of *P fluorescens* in liquid at 28° C. are shown in FIG. 7. The results indicate that at 28° C., treatments with glycerol, trehalose, and sucrose all have the potential to improve survivability of *P fluorescens*.

Figure 8:
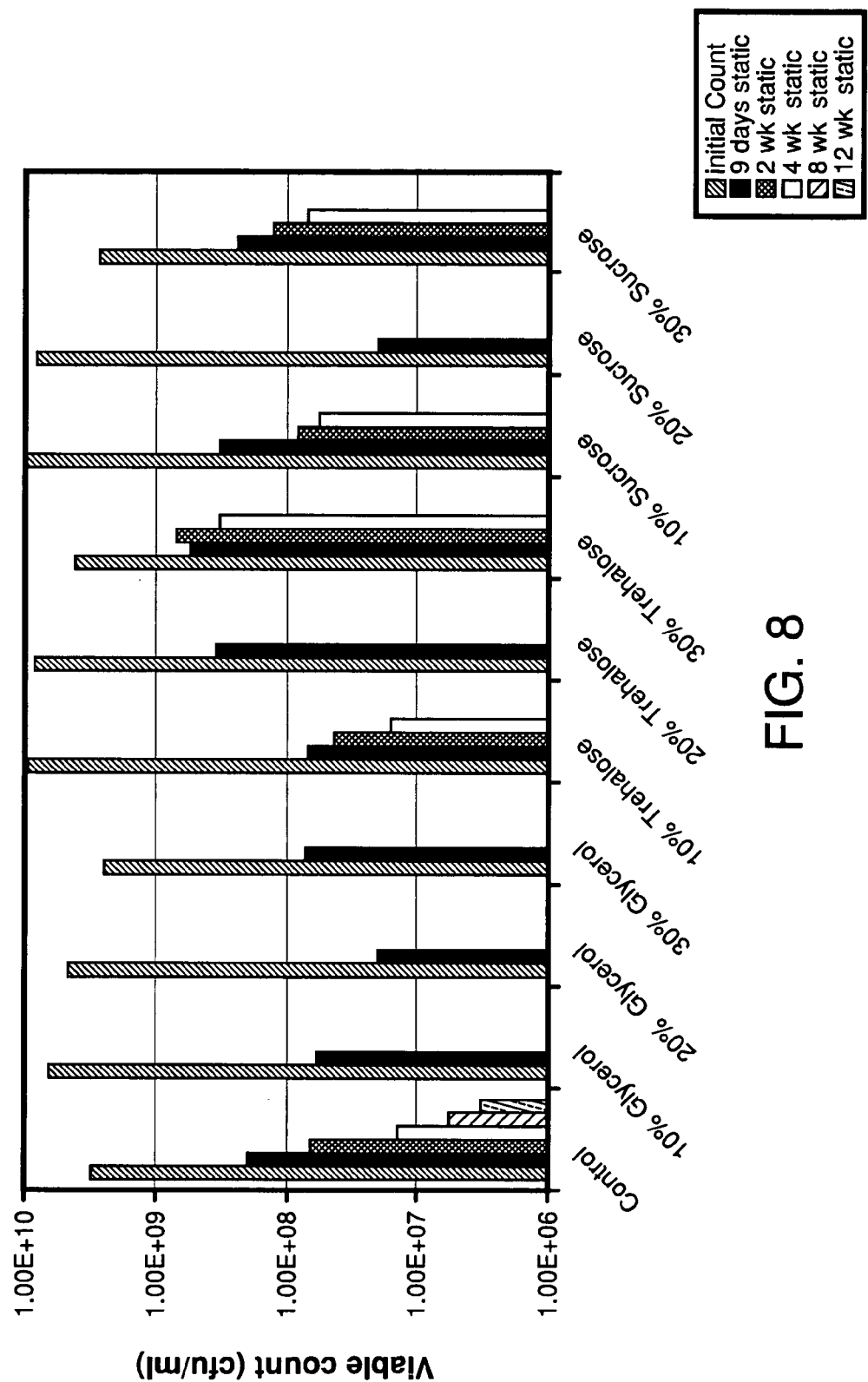
FIG. 8 is a graph of *S proteomaculans* ("*S proteomaculans*") survival in a liquid broth, as a function of the type and amount of desiccant, resulting from the practice of several embodiments of the present invention.

The results of the treatments with regard to survival of *S proteomaculans* in liquid at 28° C. are shown in FIG. 8. The results show that for up to 4 weeks, the 30% trehalose treatment, the 10% sucrose treatment, and the 30% sucrose treatment survival counts greater than the control. This data indicates that the treatments have the potential to improve survivability of *S proteomaculans*.

Example 4

Effect of Low Volume Application Rate on "On-Seed" Survival Plus a Comparison with a Commercial Product A partially desiccated inoculant product was prepared according to Example 1. The product included *B japonicum*, 20% trehalose, and 2% S-630. The product was stored in 500 ml bladders without air for four months at 5° C. before being applied to seeds.

The partially desiccated product was applied to soybean seeds (12% moisture). The seeds were treated with a total volume (partially desiccated inoculant product plus water) of 4 fluid ounces per 100 pounds of seed. The treatment was prepared by using various volumes of concentrate (1 to 4 fluid ounces per 100 pounds of seed) mixed with the appropriate amount of water to bring the total volume up to 4 fluid ounces per 100 pounds of seed. Once treated, the seeds were shaken in a bag to ensure even coverage. The bag was left open and the seeds were stored at ambient temperature (18° C. to 20° C.).

Seeds were also treated with two commercial liquids. Commercial Liquid A, a soybean inoculant having an undisclosed additive, was applied at a rate of 5.0 floz/cwt. Commercial Liquid A was ApexPro[4], a liquid soybean inoculant manufactured by Agribiotics, Inc. Commercial Liquid B, a soybean inoculant having an undisclosed additive, was applied at a rate of 4.25 floz/cwt. Commercial Liquid B was Cell-Tech® SCI™, a liquid soybean inoculant manufactured by Nitragin, Inc.

To sample the seeds, 50 seeds were selected at random using a sterilized spatula, and transferred to a sterile 100 ml medical flat containing RO water. The seeds were vigorously shaken for 1 minute. A 1000 µl sample was aseptically taken and transferred to a 9 ml McCartney bottle.

Using aseptic technique, serial dilutions of the suspension were prepared as follows: (1) immediately after shaking the 100 ml bottle, 1 ml of suspended bacteria and diluent was aseptically transferred into a first 9 ml dilution tube of RO water, thereby creating a $10^{-1}$ dilution (2) the $10^{-1}$ dilution was vortexed for 15 seconds, (3) immediately after vortexing, 1 ml of the $10^{-1}$ dilution was transferred into another 9 ml dilution tube of RO water to create a $10^{-2}$ dilution (4) the $10^{-2}$ dilution was then vortexed; (5) steps (3) and (4) were repeated to achieve $10^{-3}$ and $10^{-4}$ dilutions.

Colony assessment agar plates (Yeast Mannitol Agar) were then labelled with the details of the dilution tube used, treatment details, and plating date. Duplicate plates were created for each dilution. Prior to taking a sample from the dilution tubes and placing them on the agar plates, the dilutions were vortexed. Then, using standard aseptic pipetting techniques, 100 µL samples of each of the dilutions were dispensed centrally onto each agar plate. Using a sterile spreader, the samples were spread evenly over the surfaces of the plates. The plates were then incubated for 5-6 days at 28° C. After incubation, the number of colony forming units (CFU) on each plate were counted and recorded. Then, the following calculation was used to determine the number of CFU/plate: [Mean colonies×{labelled dilution×$10^{(a)}$×$100^{(b)}$}/$100^{(c)}$], where (a) is the correction value for 0.1 ml/plate from dilution, (b) is the correction value for 100 ml in original dilution bottle, and (c) is the correction value for number of seeds in original sample.

Figure 9:
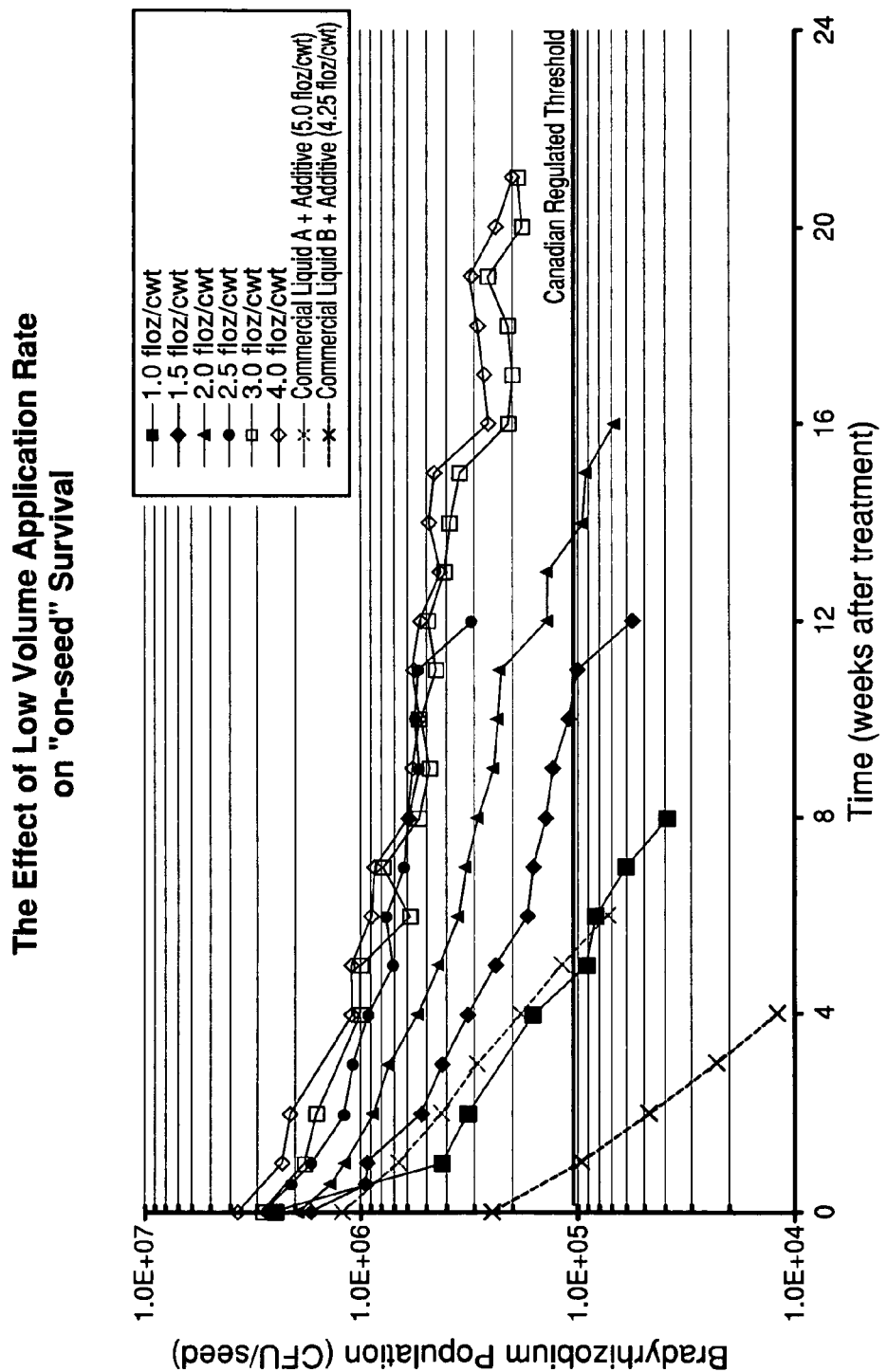
FIG. 9 is a graph of *Bradyrhizobium* population, as function of time, resulting from the practice of several embodiments of the present invention.

The results of the on-seed survival are shown in FIG. 9. The results indicate that a minimum 2 fluid ounce concentrate of the partially desiccated inoculant of the present invention (applied in a total of 4 fluid ounce per 100 pounds of seed) achieves on seed stability exceeding $10^5$ CFU/seed more than 6 weeks after treatment. The results also show that the on seed survival with the partially desiccated inoculant product of the present invention is superior to that of the two commercial liquids tested.

Example 5

Effect of Low Volume Application Rate on "On-Seed" Survival Plus Comparison with Commercial Product The same procedures were followed as in Example 4, except that the inoculant product contained 1% S-630 (and not 2% S-630), the product was stored in 3.1 L bladders (and not 500 ml bladders), and the seeds were stored at a constant 20° C. (and not 18° C. to 20° C.).

Figure 10:
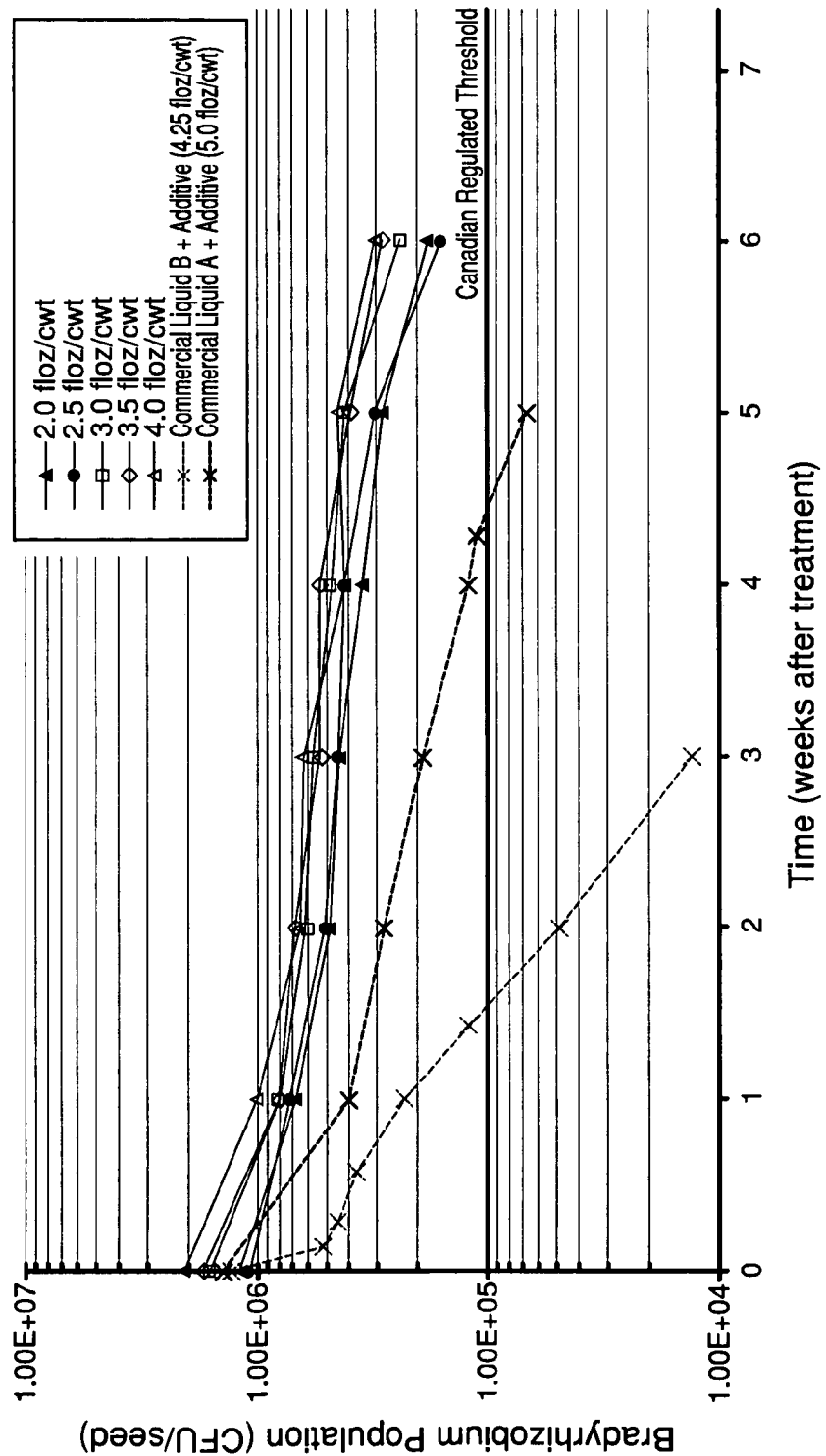
FIG. 10 is a graph of *Bradyrhizobium* population, as function of time, resulting from the practice of several embodiments of the present invention.

The results of the on-seed survival are shown in FIG. 10. The results indicate that a minimum 2 fluid ounce concentrate of the partially desiccated inoculant of the present invention (applied in a total of 4 fluid ounce per 100 pounds of seed) achieves on seed stability exceeding $10^5$ CFU/seed more than 6 weeks after treatment. The results also show that the on seed survival with the partially desiccated inoculant product of the present invention is superior to that of the two commercial liquids tested.

Example 6

Pesticide Compatibility Studies

The procedure followed for the preparation of the flasks was the same as in Example 1. The treatment for this example includes: 30% trehalose and 1% S-630.

The treatment was applied to seeds in three different manners. The first test applied only the partially desiccated inoculant product to seeds. The results for this test are shown in Table 6. The second and third tests applied the partially desiccated inoculant product and a pesticide to seeds. The pesticide in the second test was APRONMAXX RTA and was applied at an application rate of 5 fl oz./cwt. The pesticide in the third test was CRUISERMAXX and was applied at an application rate of 3 fl oz./cwt.

In both the second and third tests, the pesticides were added in three ways: tank mix, sequential, and simultaneous. The results for the second test are shown in Table 7 and the results for the third test are shown in Table 8.

For tank mix, the indicated fl oz./cwt application rate of the partially desiccated inoculant product was tank mixed for 4 hours at 20° C. with the labeled rate of pesticide. After the mixing time, the combination inoculant product/pesticide was applied to the seed at the cumulative fl oz./cwt rate.

For sequential, the pesticide was applied to the seeds at labeled rates, and allowed to dry. The partially desiccated inoculant product was then applied at indicated fl oz./cwt application rate along with a water volume to bring total rate to 4 fl oz./cwt (e.g., 2 fl oz./inoculant product+2 fl oz. water).

For simultaneous, the partially desiccated inoculant product and the pesticide were applied to the seed at the same time. The pesticide was applied to seed at the labeled rates. The partially desiccated inoculant product was applied at indicated fl oz./cwt application rate (e.g., 2 fl oz./cwt).

The "On-seed Shelf Life" noted in Tables 6-8 is the number of days, after the partially desiccated inoculant product is applied to the seeds, that the *rhizobium* count/seed exceeded a threshold level of 1×$10^5$ *rhizobium*/seed (the current Canadian regulatory threshold).

TABLE 6

Application of Partially Desiccated Inoculated Product Without Pesticide

| Application Rate* (Floz/cwt) | On-seed Shelf Life (70° F./20° C.) |
|---|---|
| 2.0 | 50 days |
| 2.5 | 55 days |
| 3.0 | 65 days |
| 3.5 | 75 days |
| 4.0 | 85 days |

*Volume to 4 fl oz./cwt with water

TABLE 7

Application of Partially Desiccated Inoculated Product and APRONMAXX RTA (5 floz/cwt)

| Application Rate | On-seed Shelf Life (70° F./20° C.) | | |
|---|---|---|---|
| (Floz/cwt) | Simultaneous | Sequential | 4 Hr Tank Mix |
| 2.0 | 10 days | 4 days | <1 day |
| 2.5 | 12 days | 5 days | 1 day |

TABLE 7-continued

Application of Partially Desiccated Inoculated Product
and APRONMAXX RTA (5 floz/cwt)

| Application Rate | On-seedShelf Life (70° F./20° C.) | | |
|---|---|---|---|
| (Floz/cwt) | Simultaneous | Sequential | 4 Hr Tank Mix |
| 3.0 | 14 days | 7 days | 2 days |
| 3.5 | 16 days | 8 days | 8 days |
| 4.0 | 18 days | 12 days | 10 days |

TABLE 8

Application of Partially Desiccated Inoculated Product
CRUISERMAXX (3 floz/cwt)

| Application Rate | On-seedShelf Life (70° F./20° C.) | | |
|---|---|---|---|
| (Floz/cwt) | Simultaneous | Sequential | 4 Hr Tank Mix |
| 2.0 | 25 days | 4 days | 1 day |
| 2.5 | 28 days | 6 days | 3 days |
| 3.0 | 30 days | 10 days | 8 days |
| 3.5 | 35 days | 14 days | 21 days |
| 4.0 | 42 days | 16 days | 25 days |

Example 7

Sugar/Sugar Alcohol Study

Partially desiccated inoculant products were prepared by first growing *Rhizobium leguminosarum* in a *Rhizobium leguminosarum* bv. *viceae* culture medium. Two different culture mediums were used, 1×R1 and 1.5×R1, which are pea and lentil fermentation medium. The 1.5×R1 has 50% more media components than 1×R1. After 3 days culture growth, a sugar or a sugar alcohol was aseptically added to the culture. The amount of sugar or sugar alcohol added to the culture is shown in final concentration (weight/volume) in Table 9 below. The culture was then allowed a 2 day conditioning phase during which the culture continued to grow thereby creating the partially desiccated inoculant product. The partially desiccated inoculant product was then applied to pea seeds at a rate of 3.1 L inoculant product/1136 kg seed. The seeds were then mixed in a bag by shaking to evenly distribute the inoculant product on the seeds. The seeds were then stored at 15° C.

As shown in Table 9 below, bacteria counts on the seeds were conducted 6 days, 12 days, 18 days, and 29 days after the inoculant was applied to the seeds. The bacteria counts were performed in a similar manner as the previous examples. That is, 50 seeds were put in 100 ml of phosphate buffer in a dilution bottle. The bottle was shaken for 5 minutes. 10 fold serial dilutions were made and 0.1 ml of proper dilution was spread onto nutrient medium plates. The viable bacteria cells on seed were calculated based on the colony numbers on the plates.

TABLE 9

| Treatment | Cfu/ml @ T = 0 | Number of Rz per seed at Days after Inoculation | | | |
|---|---|---|---|---|---|
| | | 6 days | 12 days | 18 days | 29 days |
| 1 × R1 CK | 1.86E+06 | 2.70E+05 | 1.65E+05 | 7.50E+04 | — |
| 1.5 × R1 CK | 1.24E+06 | 2.45E+05 | 2.10E+05 | 6.40E+04 | — |

TABLE 9-continued

| Treatment | Cfu/ml @ T = 0 | Number of Rz per seed at Days after Inoculation | | | |
|---|---|---|---|---|---|
| | | 6 days | 12 days | 18 days | 29 days |
| 1 × R1/20% Sorb | 9.26E+05 | 4.66E+05 | 3.40E+05 | 2.74E+05 | 1.23E+05 |
| 1 × R1/30% Sorb | 6.34E+05 | 4.50E+05 | 2.70E+05 | 2.06E+05 | 9.67E+04 |
| 1.5 × R1/20% Sorb | 1.04E+06 | 3.55E+05 | 2.02E+05 | 1.64E+05 | 8.00E+04 |
| 1.5 × R1/30% Sorb | 6.86E+05 | 3.23E+05 | 2.50E+05 | 1.84E+05 | 5.73E+04 |
| 1 × R1/20% Suc | 7.66E+05 | 6.10E+04 | 4.50E+04 | 2.22E+04 | — |
| 1 × R1/30% Suc | 9.14E+05 | 7.20E+04 | 7.70E+04 | 3.22E+04 | — |
| 1.5 × R1/20% Suc | 1.20E+06 | 1.03E+05 | 5.00E+04 | 1.92E+04 | — |
| 1.5 × R1/30% Suc | 9.14E+05 | 6.30E+04 | 4.80E+04 | 2.10E+04 | — |
| 1 × R1/20% Treh | 4.14E+05 | 7.30E+04 | 2.60E+04 | 2.36E+04 | — |
| 1 × R1/30% Treh | 5.20E+05 | 7.50E+04 | 9.30E+04 | 4.04E+04 | — |
| 1.5 × R1/20% Treh | 5.94E+05 | 7.10E+04 | 4.50E+04 | 4.38E+04 | — |
| 1.5 × R1/30% Treh | 2.74E+05 | 4.00E+04 | 6.60E+04 | 5.48E+04 | — |

The results suggest that sorbitol is the top performing sugar or sugar alcohol candidate of those tested with regards to extension of on-seed shelf life of *Rhizobium leguminosarum*.

Example 8

Sorbitol Study with 20% Sorbitol

Following on from Example 7, 20% sorbitol was selected for further evaluation with and without gellan gum ("GG") (Kelcogel F Low Acyl). The following steps were performed:
1. Grew *Rhizobium leguminosarum* in 1.5×R1 medium for 2 days at 30° C. 160 rpm.
2. Inoculated 1% of this mother culture to 1.5×R1 medium (3.41 L), 30° C., 0.1 vvm, 150 rpm, pH 6.6-7.4
3. After 3 days growth, 20% of sorbitol (final concentration w/v) was added to the fermenter, with the fermentation/conditioning process continuing for a further 2 days prior to harvest. (83% Sorbitol=83 g+46 ml $H_2O$)
4. Added gellan gum (0.1%) to 3 bags at harvest.
5. Stored the culture at 4° C.-5° C.
6. Added 1% S-630 to the broth before applying to the seed. 2.7 ml/kg.
7. Applied partially desiccated inoculant product to pea seeds at a rate of 3.1 L inoculant product/1136 kg seed.
8. Mixed the seeds in a bag by shaking to evenly distribute the inoculant product on the seeds.
9. Stored the seeds at 15° C. and 20° C.

Figure 11:
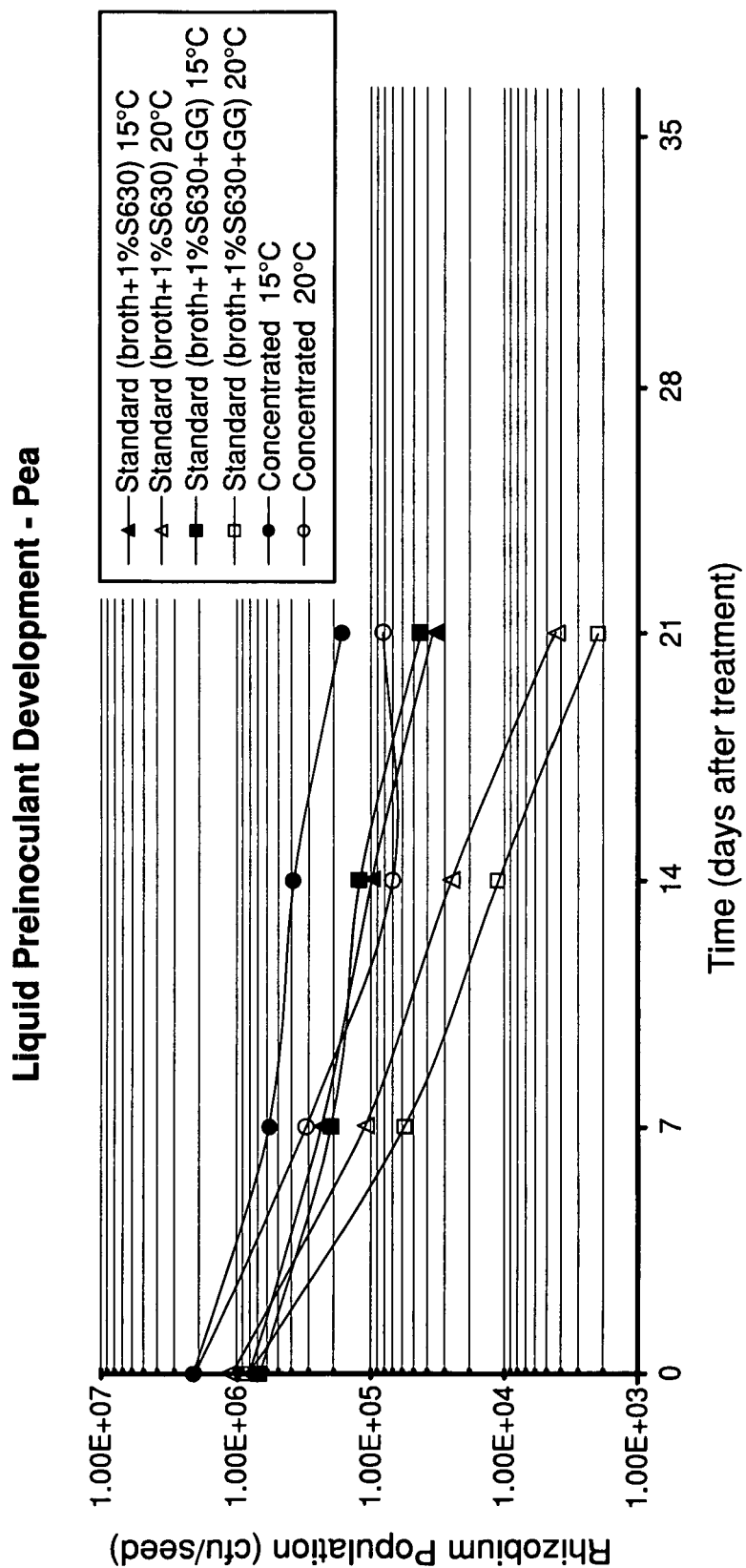
FIG. 11 is a graph of *Rhizobium* population, as function of time, resulting from the practice of several embodiments of the present invention.

The results of the tests are shown in FIG. 11. The standard formulations noted in FIG. 11 were the cultures prepared as described above. The concentrates noted in FIG. 11 were centrifuged to a pellet, and an equal volume of cell culture broth as described replaced the supernatant. Thus, the cell concentration was doubled—though all other formulatory parameters remained constant. Application rates for both formulations were 4.2 fl oz./cwt (no water).

Figure 12:
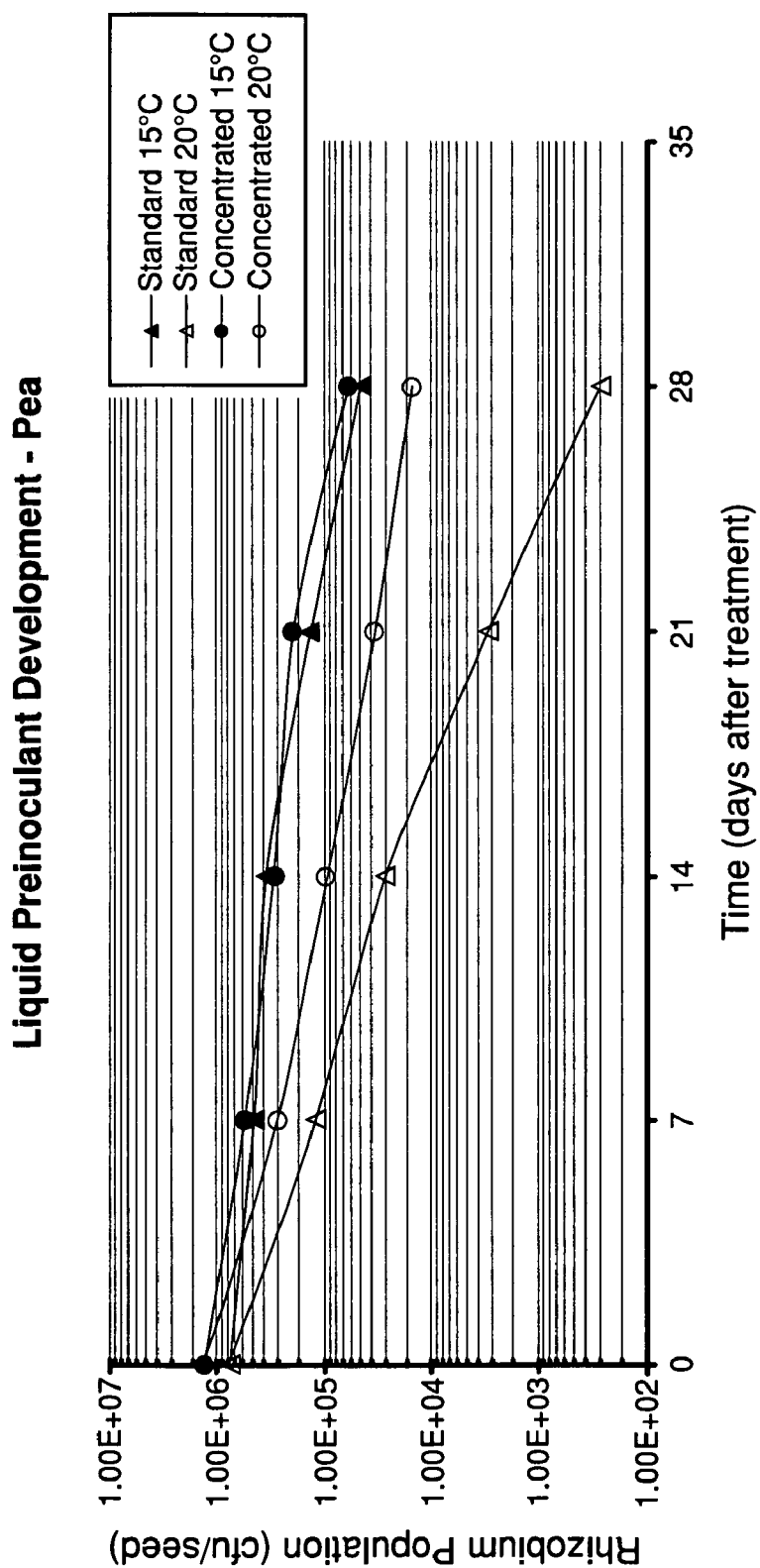
FIG. 12 is a graph of *Rhizobium* population, as function of time, resulting from the practice of several embodiments of the present invention.

Certain of the treatments (i.e., the standard formulations that did not include gellan gum) were set up in duplicate. Results from those tests are shown in FIG. 12. Based on the results, on-seed stability temperatures are critical, with a 15° C. temperature extending on-seed shelf life compared to 20° C.

Example 9

Sorbitol versus Trehalose with Soybeans

Figure 13:
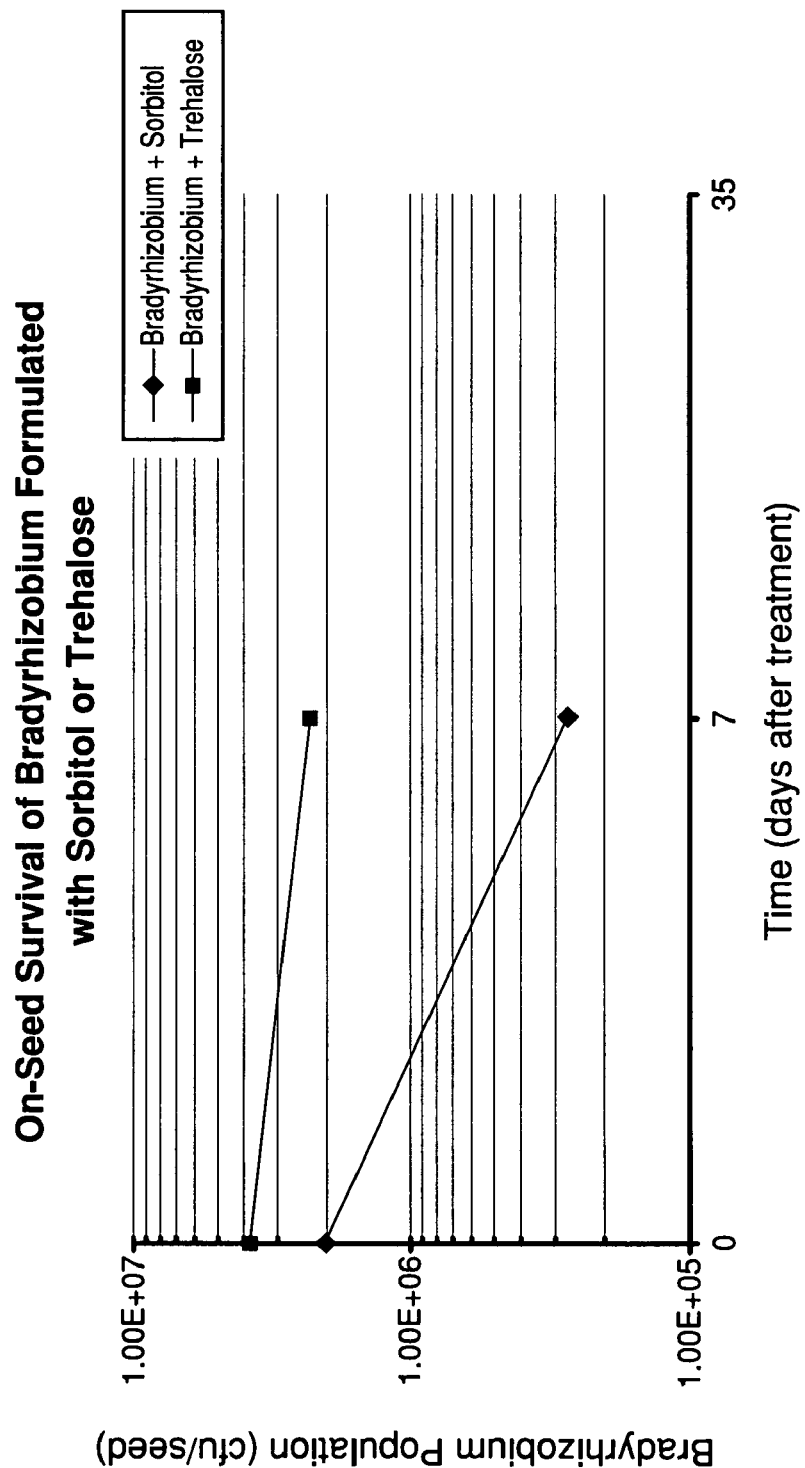
FIG. 13 is a graph of *Bradyrhizobium* population, as function of time, resulting from the practice of several embodiments of the present invention.

An experiment was run to determine whether sorbitol or trehalose is better suited for application to soybean seeds with *B japonicum*. The following steps were performed:
1. *B. japonicum* strain 532C was grown for 5 days in 1.5×Bj2 (a soybean fermentation medium) at 30° C. and 165 rpm.
2. Either sorbitol (20% w/v) or trehalose (30% w/v) was added to the culture, and the cultures were maintained for 5 days at 30° C., 165 rpm.
3. 2.7 ml/kg of either sorbitol or trehalose amended culture was applied to soybean seed. Seeds were evenly coated.
4. Seeds were stored at 18-20° C.
5. On-seed rhizobial viability was monitored at time zero and after 7 days The results of the tests are shown in FIG. 13. Based on the results, trehalose is better suited than sorbitol for application to *B japonicum*.

Example 10

Application of a Multi-Component Inoculant Composition onto a Soybean Seed

An experiment was run to determine the impact of cell concentration and ultra low trehalose amended rhizobial inoculant application on soybean on-seed survival. The following steps were performed:
1. *B. japonicum* strain 532c was cultured in 100 L nutrient medium for 7 days at 28° C. The 100 L was then microfiltered to 5 liters, and made up to 10 L through the addition of water+30% w/v* trehalose, 1% S630 w/v* and 0.05% w/v gellan gum (*w/v in final 10 L) to form a "super concentrate" broth. The super concentrate broth was fermented for a further 7 days prior to aseptic packaging. The concentration of *B. japonicum* in the super concentrate broth was $2.7 \times 10^{11}$ cfu/ml. The broth was stored at 5° C. prior to application.
2. 90 liters of a mixture of trehalose (30% w/v), S630 (1% w/v) and gellan gum (0.05% w/v) was sterilized, and aseptically packaged as a "conditioner." The harvested conditioner units were stored at 20° C. prior to application.
3. 0.2 fl oz. of the super concentrate, 1.8 fl oz. of the conditioner, and 3 fl oz. of water were mixed. The concentration of *B. japonicum* in the mixture was $7.4 \times 10^9$ cfu/ml. This mixture was applied on a pro rata basis to 100 lbs soybean seed.
4. Inoculated seed were stored at 15° C. and 20° C., and assessed at weekly intervals using the methodology described above.

The results from the tests are shown in Table 10 and FIG. 14.

TABLE 10

| Assessment Time (Weeks after Treatment) | Cfu/Seed At Weeks After Treatment | |
|---|---|---|
| | Seeds @ 15° C. | Seeds @ 20° C. |
| 0 | $2.4 \times 10^6$ | $1.9 \times 10^6$ |
| 1 | $1.2 \times 10^6$ | $1.3 \times 10^6$ |
| 2 | $9.9 \times 10^5$ | $9.2 \times 10^5$ |
| 3 | $9.8 \times 10^5$ | $8.9 \times 10^5$ |
| 4 | $9.8 \times 10^5$ | $7.1 \times 10^5$ |

It will be appreciated by those skilled in the art, that the present invention may be practiced in various alternate forms and configurations. The previously detailed description of the disclosed embodiments is presented for purposes of clarity of understanding only, and no unnecessary limitations should be implied there from.

We claim:
1. A method for preparing a partially desiccated liquid inoculant product, the method comprising:
providing a liquid inoculant comprising bacteria from one or more of genera *Rhizobium, Bradyrhizobium, Pseudomonas* or *Serratia* grown to a substantially stationary phase;
adding to the liquid inoculant, in an amount sufficient to partially desiccate the liquid inoculant, a desiccant treatment comprising a desiccant to form a partially desiccated liquid inoculant product, wherein the desiccant comprises from about 5% to about 50% by weight/volume of the partially desiccated liquid product and wherein the desiccant comprises one or more of trehalose, sucrose, glycerol or sorbitol; and
allowing the partially desiccated liquid inoculant product to enter a conditioning phase, wherein the conditioning phase is about 1 day to about 10 days.

2. The method according to claim 1 wherein the conditioning phase is about 2 to about 3 days.

3. A method for preparing a partially desiccated liquid inoculant product, the method comprising:
providing a liquid inoculant comprising bacteria from one or more of the genera *Rhizobium, Bradyrhizobium, Pseudomonas* or *Serratia*, said bacteria grown to a substantially stationary phase;
adding to the liquid inoculant, in an amount sufficient to partially desiccate the liquid inoculant, a desiccant treatment comprising a desiccant to form a partially desiccated liquid inoculant product, wherein the desiccant comprises from about 5% to about 50% by weight/volume of the partially desiccated liquid product, and wherein the desiccant comprises one or more of trehalose, sucrose, glycerol or sorbitol; and
allowing the partially desiccated liquid inoculant product to enter a conditioning phase, wherein the conditioning phase is about 1 day to about 10 days; and
packaging the partially desiccated liquid inoculant product.

4. The method according to claim 3 wherein the method further comprises storing the partially desiccated liquid inoculant product.

5. A method of applying a partially desiccated liquid inoculant product to a seed, the method comprising:
providing a liquid inoculant comprising bacteria from one or more of genera *Rhizobium, Bradyrhizobium, Pseudomonas* or *Serratia*, said bacteria grown to a substantially stationary phase;
adding to the liquid inoculant a desiccant treatment comprising a desiccant to form the partially desiccated liquid inoculant product, wherein the desiccant comprises from about 5% to about 50% by weight/volume of the partially desiccated liquid product, and wherein the desiccant comprises one or more of trehalose, sucrose, glycerol or sorbitol; and
allowing the partially desiccated liquid inoculant product to enter a conditioning phase, wherein the conditioning phase is about 1 day to about 10 days; and applying the partially desiccated liquid inoculant product to the seed at a rate of about 1.5 fluid ounces/hundred pounds of seed to about 4.0 fluid ounces/hundred pounds of seed.

6. The method according to claim 5 wherein the partially desiccated liquid inoculant product is applied to the seed as a mixture, the mixture comprising the partially desiccated liquid inoculant product and one or more of water and a cidal compound.

7. The method according to claim 6 wherein the partially desiccated liquid inoculant product and water are applied to the seed at a combined rate of about 3.5 fluid ounces/hundred pounds of seed to about 6.0 fluid ounces/hundred pounds of seed.

8. The method according to claim 5 wherein the partially desiccated liquid inoculant product is applied at a rate of 2.0 fluid ounces/hundred pounds of seed to about 3.2 fluid ounces/hundred pounds of seed.

9. The method according to claim 6 wherein the mixture comprises the partially desiccated liquid inoculant product and at least one cidal compound.

10. The method according to claim 9 wherein the at least one cidal compound comprises one or more of insecticides, fungicides, herbicides, bactericides, pesticides, virucides, acaracides, miticides, nematicides, rodenticides, or combinations thereof.

11. The method according to claim 9 wherein the partially desiccated liquid inoculant product is applied at a rate of 2.0 fluid ounces/hundred pounds of seed to about 3.2 fluid ounces/hundred pounds of seed.

12. The method according to claim 5, wherein the desiccant consists of trehalose and one or more of sucrose, glycerol and sorbitol.

13. The method according to claim 12 wherein the trehalose is from about 10% to about 40% by weight/volume of the partially desiccated liquid inoculant product.

14. The method according to claim 13 wherein the trehalose is from about 20% to about 30% by weight/volume of the partially desiccated liquid inoculant product.

15. The method according to claim 5 wherein the seed comprises a seed for a leguminous plant.

16. The method according to claim 5 wherein the number of bacteria on the seed after about 10 weeks on the seed exceeds about $1\times10^5$.

17. The method according to claim 5 wherein the method further comprises applying an extender to the seed after the partially desiccated liquid inoculant product is applied.

18. A method of applying a partially desiccated liquid inoculant product to a seed, the method comprising:
providing a liquid inoculant comprising bacteria from one or more of genera *Rhizobium, Bradyrhizobium, Pseudomonas* or *Serratia*, said bacteria grown to a substantially stationary phase;
adding to the liquid inoculant, in an amount sufficient to partially desiccate the liquid inoculant, a desiccant treatment comprising a desiccant to form the partially desiccated liquid inoculant product, wherein the desiccant comprises from about 5% to about 50% by weight/volume of the partially desiccated liquid product and wherein the desiccant is one or more of trehalose, sucrose, glycerol or sorbitol; and
allowing the partially desiccated liquid inoculant product to enter a conditioning phase, wherein the conditioning phase is about 1 day to about 10 days; and
applying a conditioner and the partially desiccated liquid inoculant product to the seed, wherein the partially desiccated liquid inoculant product comprises at least $1\times10^{11}$ cfu/ml of bacteria.

19. The method according to claim 18 wherein the conditioner comprises at least one polymer comprising one or more of polyvinyl pyrrolidone, alkylated vinyl pyrrolidone polymers, vinyl pyrrolidone and vinyl acetate copolymers, vinyl pyrrolidone and styrene copolymers, and polyvinyl alcohol polymers.

20. The method according to claim 19 wherein the bacteria concentration in the partially desiccated liquid inoculant product is $1\times10^{11}$ cfu/ml to about $1\times10^{12}$ cfu/ml.

21. The method according to claim 19 wherein the conditioner further comprises at least one desiccant.

22. The method according to claim 21 wherein the conditioner further comprises water.

23. The method according to claim 18 wherein the partially desiccated liquid inoculant product is applied at an application rate of about 0.1 fluid ounces/hundred pounds of seed to about 0.5 fluid ounces/hundred pounds of seed and the conditioner is applied at an application rate of about 1.2 fluid ounces/hundred pounds of seed to about 2.5 fluid ounces/hundred pounds of seed.

24. The method according to claim 23 wherein the partially desiccated liquid inoculant product is applied at an application rate of about 0.2 fluid ounces/hundred pounds of seed and the conditioner is applied at an application rate of about 1.8 fluid ounces/hundred pounds of seed.

25. A method of treating seeds, the method comprising:
administering a partially desiccated liquid inoculant product prepared according to claim 1 onto the seeds; and
administering a cidal compound onto the seeds;
wherein the application rate of the liquid inoculant product and the cidal compound together is less than 9.2 fluid ounces/hundred pounds of seed.

26. A method according to claim 25 wherein the cidal compound comprises one or more of an one or more of insecticides, fungicides, herbicides, bactericides, pesticides, virucides, acaracides, miticides, nematicides, rodenticides, or combinations thereof.

27. A method according to claim 25 wherein the seeds are selected from the group consisting of seeds from soybean, lucerne, peanut, peas, lentils, and beans.

28. A method according to claim 25 wherein the application rate of the liquid inoculant product and the cidal compound together is less than 5.0 fluid ounces/hundred pounds of seed.

29. A method according to claim 25 wherein the liquid inoculant product is applied at an application rate of less than 3.2 fluid ounces/hundred pounds of seed.

* * * * *